US007771726B2

(12) United States Patent
Tsuji et al.

(10) Patent No.: US 7,771,726 B2
(45) Date of Patent: Aug. 10, 2010

(54) USE OF SYNTHETIC GLYCOLIPIDS AS UNIVERSAL ADJUVANTS FOR VACCINES AGAINST CANCER AND INFECTIOUS DISEASES

(75) Inventors: Moriya Tsuji, New York, NY (US); John Schmieg, New York, NY (US); Richard Franck, Riverside, CT (US); Yaoxing Huang, Brooklyn, NY (US)

(73) Assignees: New York University, New York, NY (US); The Research Foundation of the City University of New York, New York, NY (US); Aaron Diamond Aids Research Center, New York, NY (US)

( * ) Notice: Subject to any disclaimer, the term of this patent is extended or adjusted under 35 U.S.C. 154(b) by 692 days.

(21) Appl. No.: 10/962,374

(22) Filed: Oct. 8, 2004

(65) Prior Publication Data

US 2005/0192248 A1  Sep. 1, 2005

Related U.S. Application Data

(60) Provisional application No. 60/509,821, filed on Oct. 8, 2003.

(51) Int. Cl.
*A61K 39/39* (2006.01)
(52) U.S. Cl. .............. 424/184.1; 424/188.1; 424/191.1; 424/204.1; 424/208.1; 424/209.1; 424/232.1; 424/233.1; 424/234.1; 424/269.1; 424/274.1
(58) Field of Classification Search .................. None
See application file for complete search history.

(56) References Cited

U.S. PATENT DOCUMENTS

| | | | |
|---|---|---|---|
| 5,780,441 | A | 7/1998 | Higa et al. |
| 5,849,716 | A | 12/1998 | Akimoto et al. |
| 5,936,076 | A | 8/1999 | Higa et al. |
| 6,531,453 | B1 | 3/2003 | Taniguchi et al. |
| 6,635,622 | B2 | 10/2003 | Tomiyama et al. |
| 2003/0157135 | A1* | 8/2003 | Tsuji et al. ............... 424/278.1 |

FOREIGN PATENT DOCUMENTS

| | | | |
|---|---|---|---|
| EP | 1 018 548 A1 | | 7/2000 |
| WO | WO-99/15627 A1 | | 4/1999 |
| WO | WO 01/24810 | * | 4/2001 |
| WO | WO 03/066833 | * | 8/2003 |
| WO | WO 03/105769 | * | 12/2003 |

OTHER PUBLICATIONS

Moingeon (Journal of Biotechnology, 2002, vol. 98, pp. 189-198).*
Abstract of Cohen (Proceedings of the Royal Society of London, B, 1978, vol. 203, pp. 323-346).*
Abstract of Hoffman et al (Immunology Letters, 1990, vol. 25, pp. 33-38).*

Junqing Cui, "Inhibition of T Helper Cell Type 2 Cell Differentiation and Immunoglobulin E Response by Ligand-activated Vα14 Natural Killer T Cells," *J. Exp. Med.* 190(6):783-792 (Sep. 20, 1999).

Gloria Gonzalez-Aseguinolaza et al., "Natural Killer T Cell Ligand α-Galactosylceramide Enhances Protective Immunity Induced by Malaria Vaccines," *J. Exp. Med.* 195(5):617-624 (Mar. 4, 2002).

Gloria Gonzalez-Asequinolaza et al., "α-Galactosylceramide-activated Vα14 natural killer T cells mediate protection against murine malaria," *PNAS* 97(15):8461-8466 (Jul. 18, 2000).

Akira Hasegawa et al., "Synthesis of cerebroside, lactosyl ceramide, and ganglioside GM, analogs containing β-thioglycosidically linked ceramide," *Carbohydrate Research* 214:43-53 (1991).

Seokmann Hong et al., "The natural killer T-cell ligand α-galactosylceramide prevents autoimmune diabetes.in non-obese diabetic mice," *Nature Medicine* 7(9):1052-1056 (Sep. 2001).

Soichiro Ishihara et al., "α-Glycosylceramides Enhance the Antitumor Cytotoxicity of Hepatic Lymphocytes Obtained from Cancer Patients by Activating CD3⁻CD56⁺ NK Cells In Vitro," *The Journal of Immunology*, 165:1659-1664 (2000).

Fujii, S. et al., "Glycolipid a-C-galactosylceramide is a Distinct Inducer of Dendritic Cell Function During Innate and Adaptive Immune Responses of Mice," PNAS, Jul. 25, 2006, 103(30):11252-11257.

Gonzalez-Aseguinolaza, G. et al., "Natural Killer T Cell Ligand a-Galactosylceramide Enhances Protective Immunity Induced by Malaria Vaccines," J. Exp. Med., Mar. 4, 2002, 195(5):617-624.

Yoon, H. A. et al., "Modulation of Immune Responses Induced by DNA Vaccine Expressing Glycoprotein B of Pseudorabies Virus via Coadministration of IFN-g-Associated Cytokines," J. of Interferon & Cytokine Res., 2006, 26:730-738.

Stagg, J. et al., "Granulocyte-Macrophage Colony-Stimulating Factor and Interleukin-2 Fusion cDNA for Cancer Gene Immunotherapy," Cancer Research, Dec. 15, 2004, 64:8795-8799.

Chen, H. et al., "Suppression of Immune Response and Protective Immunity to a Japanese Encephalitis Virus DNA Vaccine by Coadministration of an IL-12-Expressing Plasmid," J. Immunol., 2001, 166:7419-7426.

Koblish, H. K. et al., "Immune Suppression by Recombinant Interleukin (rIL)-12 Involves Interferon γ Induction of Nitric Oxide Synthase 2 (iNOS) Activity: Inhibitors of NO Generation Reveal the Extent of rIL-12 Vaccine Adjuvant Effect," J. Exp. Med., Nov. 2, 1998, 188(9):1603-1610.

(Continued)

*Primary Examiner*—Karen A Canella
(74) *Attorney, Agent, or Firm*—Fish & Richardson P.C.

(57) ABSTRACT

The present invention relates to methods and compositions for augmenting an immunogenicity of an antigen in a mammal, comprising administering said antigen together with an adjuvant composition that includes a synthetic glycolipid compound of Formula I, as described herein. According to the present invention, the use of a compound of Formula I as an adjuvant is attributed at least in part to the enhancement and/or extension of antigen-specific Th1-type responses, in particular, CD8+ T cell responses. The methods and compositions of the present invention can be useful for prophylaxis and treatment of various infectious and neoplastic diseases.

38 Claims, 2 Drawing Sheets

OTHER PUBLICATIONS

Figure 1:
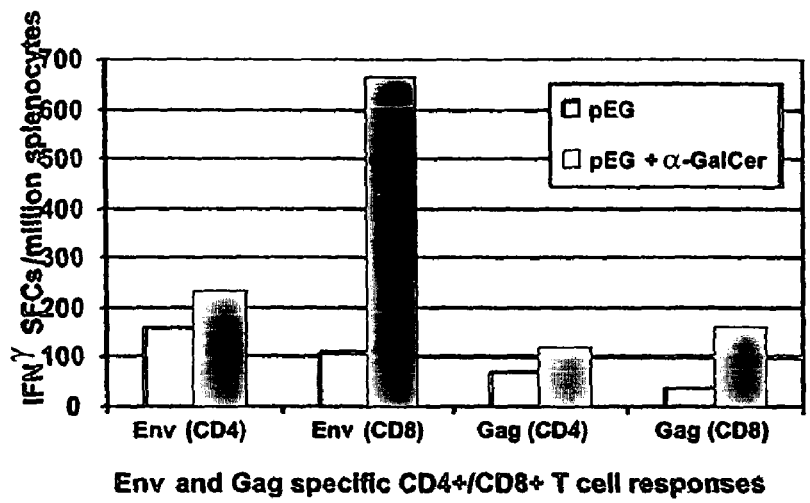

Barouch, D. H. et al., "Augmentation and Suppression of Immune Responses to an HIV-1 DNA Vaccine by Plasmid Cytokine/Ig Administration," J. Immunol., 1998, 161:1875-1882.

Fujii, S. et al., "The Linkage of Innate to Adaptive Immunity via Maturing Dendritic Cells In Vivo Requires CD40 Ligation in Addition to Antigen Presentation and CD80/86 Costimulation," J. Exp. Med., Jun. 21, 2004, 199 (12):1607-1618.

Response filed Oct. 31, 2007 in U.S. Appl. No. 10/206,155.

Declaration of Moriya Tsuji under 37 CFR 1.132 executed Mar. 26, 2008.

Mempel, T.R. et al., "T-cell Priming by Dendritic Cells in Lymph Nodes Occurs in Three Distinct Phases," Nature 2004, 427:154-159.

Hafalla, J.C. et al., "Short-term Antigen Presentation and Single Clonal Burst Limit the Magnitude of the CD8+ T Cell Responses to Malaria Liver Stages," PNAS 2002, 99:11819-11824.

Crul et al., "Population Pharmacokinetics of the Novel Anticancer Agent KRN7000," Cancer Chemother Pharmacol 2002, 49:287-293.

Huang et al., "Enhancement of HIV DNA Vaccine Immunogenicity by the NKT Cell Ligand, α-galactosylceramide," Vaccine 2008, 26: 1807-1816.

Acacia de Sa Pinheiro, A. et al. "IL-4 induces a wide-spectrum intracellular signaling cascade in $CD8^+$ T cells." J. Leukocyte Biology 2007, 81:1102-10.

Ekkens, M. et al. "Th1 and Th2 Cells Help CD8 T-Cell Responses." Infection and Immunity, May 2007, p. 2291-2296.

Hoffman, S. et al. "Irradiated sporozoite vaccine induces cytotoxic T lymphocytes that recognize malaria antigens on the surface of infected hepatocytes." Immunology Letters 1990, 25:33-38.

Morris, S. et al. "Endogenously Produced IL-4 Nonredundantly Stimulates $CD8^+$ T Cell Proliferation." J. Immunol. 2009, 182:1429-38.

Ueda, N. et al. "CD1d-restricted NKT cell activation enhanced homeostatic proliferation of $CD8^+$ T cells in a manner dependent on IL-4." Int. Immunol. 2006, 18:1397-404.

Kazuhiro Kakimi et al., "Natural Killer T Cell Activation Inhibits Hepatitis B Virus Replication In Vivo," J. Exp. Med. 192(7):921-930 (Oct. 2, 2000).

Kazuyoshi Kawakami et al., "Activation of $Vα14^+$ Natural Killer T Cells by α-Galactosylceramide Results in Development of Th1 Response and Local Host Resistance in Mice Infected with Cryptococcus neoformans," Infection and Immunity 69(1):213-220 (Jan. 2001).

Tetsu Kawano et al., "Antitumor Cytotoxicity Mediated by Ligand-activated Human Vα24 NKT Cells," Cancer Research 59:5102-5105 (Oct. 15, 1999).

Hidemitsu Kitamura et al., "The Natural Killer T (NKT) Cell Ligand α-Galactosylceramide Demonstrates Its Immunopotentiating Effect by Inducing Interleukin (IL)-12 Production by Dendritic Cells and IL-12 Receptor Expression on NKT Cells," J. Exp. Med. 189(7):1121-1127 (Apr. 5, 1999).

Eiichi Kobayashi et al., "KRN7000, A Novel Immunomodulator, and Its Antitumor Activities," Oncology Research 7(10/11):529-534 (1995).

Katsuichi Miyamoto et al., "A synthetic glycolipid prevents autoimmune encephalomyelitis by inducing $T_H2$ bias of natural killer T cells," Nature 413:531-534 (Oct. 4, 2001).

Ryusuke Nakagawa et al., "Treatment of Hepatic Metastasis of the Colon26 adenocarcinoma with an α-Galactosylceramide, KRN7000," Cancer Research 58:1202-1207 (Mar. 15, 1998).

Takashi Nishimura et al., "The interface between innate and acquired immunity: glycolipid antigen presentation by CD1d-expressing dendritic cells to NKT cells induces the differentiation of antigen-specific cytotoxic T lymphocytes," International Immunology 12(7):987-994 (Mar. 7, 2000).

Shayan Sharif, "Activation of natural killer T cells by α-galactosylceramide treatment prevents the onset and recurrence of autoimmune Type 1 diabetes," Nature Medicine 7(9):1057-1062 (Sep. 2001).

Akihiro Shimosaka et al., "KRN7000: A Novel Dendritic Cell Activator," Abstract 6, pp. 21-22, First International Workshop, Cell Therapy: Filing the Gap Between Basic Science and Clinical Trials, Abstract Book, Istituto Superiore di Sanità, Rome (Oct. 15-17, 2001).

Nagendra Singh et al., "Cutting Edge: Activation of NK T Cells by CD1d and α-Galactosylceramide Directs Conventional T Cells to the Acquisition of a Th2 Phenotype," The Journal of Immunology 2373-2377 (1999).

Michael T. Wilson et al., "Immunotherapy with ligands of natural killer T cells," Trends in Molecular Medicine 8(5):225-231 (May 2002).

* cited by examiner

Adjuvant Effects of α-GalCer on DNA Vaccination in Mice: Enhancement of HIV-Specific CD4+/CD8+ T Cell Responses CRONY-101 exhibits more potent adjuvant activity than α-GalCer, enhancing a malaria-specific CD8+ T cell response elicited by a recombinant adenovirus expressing a malaria antigen CRONY-101 exhibits more potent adjuvant activity than α-GalCer, enhancing a Gag-specific CD8+ T cell response elicited by a DNA vaccine encoding a HIV-Gag sequence CRONY-101 exhibits more potent adjuvant activity than α-GalCer, enhancing a Gag-specific CD4+ T cell response elicited by a DNA vaccine encoding a HIV-Gag sequence

USE OF SYNTHETIC GLYCOLIPIDS AS UNIVERSAL ADJUVANTS FOR VACCINES AGAINST CANCER AND INFECTIOUS DISEASES

This application claims priority from U.S. Provisional Application Ser. No. 60/509,821 filed Oct. 8, 2003, which is hereby incorporated by reference.

This invention was made with government support under grant number R21 AI47840-01A1, awarded by the National Institute of Health/National Institute of Allergy and Infectious Diseases, and grant number R01 GM 60271, awarded by the National Institute of Health/General Medical Sciences. Accordingly, the United States Government has certain rights in the invention.

FIELD OF THE INVENTION

The present invention relates to the use of α-C-galactosyl ceramides (α-C-GalCer) synthetic glycolipids as adjuvants to augment the immunogenicity of various infectious and tumor antigens.

BACKGROUND OF THE INVENTION

The successful elimination of pathogens, neoplastic cells, or self-reactive immune mechanisms following prophylactic or therapeutic immunization depends to a large extent on the ability of the host's immune system to become activated in response to the immunization and mount an effective response, preferably with minimal injury to healthy tissue.

The rational design of vaccines initially involves identification of immunological correlates of protection—the immune effector mechanism(s) responsible for protection against disease—and the subsequent selection of an antigen that is able to elicit the desired adaptive response. Once this appropriate antigen has been identified, it is essential to deliver it effectively to the host's immune system.

In the design of effective vaccines, immunological adjuvants serve as critical components, which accelerate, prolong, and/or enhance an antigen-specific immune response as well as provide the selective induction of the appropriate type of response.

New vaccines are presently under development and in testing for the control of various neoplastic, autoimmune and infectious diseases, including human immunodeficiency virus (HIV) and tuberculosis. In contrast to older vaccines which were typically based on live-attenuated or non-replicating inactivated pathogens, modern vaccines are composed of synthetic, recombinant, or highly purified subunit antigens. Subunit vaccines are designed to include only the antigens required for protective immunization and are believed to be safer than whole-inactivated or live-attenuated vaccines. However, the purity of the subunit antigens and the absence of the self-adjuvanting immunomodulatory components associated with attenuated or killed vaccines often result in weaker immunogenicity.

The immunogenicity of a relatively weak antigen can be enhanced by the simultaneous or more generally conjoined administration of the antigen with an "adjuvant," usually a substance that is not immunogenic when administered alone, but will evoke, increase and/or prolong an immune response to an antigen. In the absence of an adjuvant, a reduced or no immune response may occur, or worse the host may become tolerized to the antigen.

Adjuvants can be found in a group of structurally heterogeneous compounds (Gupta et al., 1993, Vaccine, 11:293-306). Classically recognized examples of adjuvants include oil emulsions (e.g., Freund's adjuvant), saponins, aluminium or calcium salts (e.g., alum), non-ionic block polymer surfactants, lipopolysaccharides (LPS), mycobacteria, tetanus toxoid, and many others. Theoretically, each molecule or substance that is able to favor or amplify a particular situation in the cascade of immunological events, ultimately leading to a more pronounced immunological response, can be defined as an adjuvant.

In principle, through the use of adjuvants in vaccine formulations, one can (1) direct and optimize immune responses that are appropriate or desirable for the vaccine; (2) enable mucosal delivery of vaccines, i.e., administration that results in contact of the vaccine with a mucosal surface such as buccal or gastric or lung epithelium and the associated lymphoid tissue; (3) promote cell-mediated immune responses; (4) enhance the immunogenicity of weaker immunogens, such as highly purified or recombinant antigens; (5) reduce the amount of antigen or the frequency of immunization required to provide protective immunity; and (6) improve the efficacy of vaccines in individuals with reduced or weakened immune responses, such as newborns, the aged, and immunocompromised vaccine recipients.

Although little is known about their mode of action, it is currently believed that adjuvants augment immune responses by one of the following mechanisms: (1) increasing the biological or immunologic half-life of antigens (see, e.g., Lascelles, 1989, Vet. Immunol. Immunopathol., 22: 15-27; Freund, 1956, Adv. Tuber. Res., 7: 130-147); (2) improving antigen delivery to antigen-presenting cells (APCs), as well as antigen processing and presentation by the APCs (see, e.g., Fazekas de St. Groth et al., Immunol. Today, 19: 448-454, 1998), e.g., by enabling antigen to cross endosomal membranes into the cytosol after ingestion of antigen-adjuvant complexes by APCs (Kovacsovics-Bankowski et al., Science, 1995, 267: 243-246); (3) mimicking microbial structures leading to improved recognition of microbially-derived antigens by the pathogen-recognition receptors (PRRs), which are localized on accessory cells from the innate immune system (Janeway, 1989, Cold Spring Harbor Symp. Quant. Biol., 54:1-13; Medzhitov, 1997, Cell, 91:295-298; Rook, 1993, Immunol. Today, 14:95-96); (4) mimicking danger-inducing signals from stressed or damaged cells which serve to initiate an immune response (see, e.g., Matzinger, 1994, Annu. Rev. Immunol., 12:991-209), (5) inducing the production of immunomodulatory cytokines (see, e.g., Nohria, 1994, Biotherapy, 7:261-269; Iwasaki et al., 1997, J. Immunol., 158:4591-4601; Maecker et al., 1997, Vaccine, 15:1687-1696); (6) biasing the immune response towards a specific subset of the immune system (e.g., generating Th1- or Th2-polarized response (Janssen et al., Blood, 97:2758-2763, 2001; Yamamoto et al., Scand. J. Immunol., 53:211-217, 2001; Weiner G. J., J. Leukoc. Biol., 68:455-63, 2000; Lucey, Infect. Dis. Clin. North Am., 13:1-9, 1999), and (7) blocking rapid dispersal of the antigen challenge (the "depot effect") (Hood et al., Immunology, Second Ed., 1984, Benjamin/Cummings: Menlo Park, Calif.; St Clair et al., Proc. Natl. Acad. Sci. U.S.A., 96:9469-9474, 1999; Ahao et al., J. Pharm. Sci., 85:1261-1270, 1996; Morein et al., Vet. Immunol. Immunopathol., 54:373-384, 1996). (See also reviews by Schijns, Curr. Opin. Immunol., 12: 456-463, 2000; Vogel, Clin. Infect. Dis., 30 [Suppl. 3]: S266-70, 2000; Singh and O'Hagan, Nature Biotechnol., 17: 1075-81, 1999; Cox and Coulter, Vaccine, 15: 248-256, 1997).

Recent observations strongly suggest that endogenously produced cytokines act as essential communication signals elicited by traditional adjuvants. The redundancy of the cytokine network makes it difficult to ascribe the activity of a particular adjuvant to one or more cytokines. Cytokines crucial for immunogenicity may include the proinflammatory (Type 1) substances: interferon (IFN)-α/β, tumor necrosis factor (TNF)-α, interleukin (IL-)-1, IL-6, IL-12, IL-15 and IL-18, which influence antigen presentation. Others may act more downstream during clonal expansion and differentiation of T and B cells, with IL-2, IL-4 and IFN-γ as prototypes (Brewer et al., 1996, *Eur. J. Immunol.*, 26:2062-2066; Smith et al., 1998, Immunology, 93:556-562). Adjuvants that enhance immune responses through the induction of IFN-γ and delayed-type hypersensitivity also elicit the production of IgG subclasses that are the most active in complement-mediated lysis and in antibody-dependent cell-mediated-cytotoxicity effector mechanisms (e.g., IgG2a in mice and IgG1 in humans) (Allison, *Dev. Biol. Stand.*, 1998, 92:3-11; Unkeless, *Annu. Rev. Immunol.*, 1988, 6:251-81; Phillips et al., *Vaccine*, 1992, 10:151-8).

Clearly, some adjuvants may perform more than one function. For example, purified microbial components such as LPS or extracts of *Toxoplasma gondii* rapidly increase not only the number of antigen-presenting dendritic cells (DC) and their migration but also IL-12 production (Souza et al, 1997, *J. Exp. Med.*, 186:1819-1829).

As different adjuvants may have diverse mechanisms of action, their being chosen for use with a particular vaccine may be based on the route of administration to be employed, the type of immune responses desired (e.g., antibody-mediated, cell-mediated, mucosal, etc.), and the particular inadequacy of the primary antigen.

The benefit of incorporating adjuvants into vaccine formulations to enhance immunogenicity must be weighed against the risk that these agents will induce adverse local and/or systemic reactions. Local adverse reactions include local inflammation at the injection site and, rarely, the induction of granuloma or sterile abscess formation. Systemic reactions to adjuvants observed in laboratory animals include malaise, fever, adjuvant arthritis, and anterior uveitis (Allison et al., *Mol. Immunol.*, 1991, 28:279-84; Waters et al., *Infect. Immun.*, 1986, 51:816-25). Such reactions often are caused by the interaction of the adjuvant and the antigen itself, or may be due to the type of response to a particular antigen the adjuvant produces, or the cytokine profile the adjuvant induces.

Thus, many potent immunoadjuvants, such as Freund's Complete or Freund's Incomplete Adjuvant, are toxic and are therefore useful only for animal research purposes, not human vaccinations. Currently, aluminum salts and MF59 are the only vaccine adjuvants approved for human use. Of the novel adjuvants under evaluation, immunostimulatory molecules such as the lipopolysaccharide-derived MPL and the saponin derivative QS-21 appear most promising, although doubts have been raised as to their safety for human use. Preclinical work with particulate adjuvants, such as the MF59 microemulsion and lipid-particle immuno-stimulating complexes (ISCOMs), suggest that these molecules are also themselves potent elicitors of humoral and cellular immune responses. In addition, preclinical data on CpG oligonucleotides appear to be encouraging, particularly with respect to their ability to manipulate immune responses selectively. While all these adjuvants show promise, the development of more potent novel adjuvants may allow novel vaccines to be developed and both novel and existing vaccines to be used as therapeutic as well as improved prophylactic agents.

Recently, a novel lymphoid lineage, natural killer T (NKT) cells, distinct from mainstream T cells, B cells and NK cells, has been identified (Arase et al., 1992, *Proc. Natl. Acad. Sci. USA*, 89:6506; Bendelac et al., 1997, *Annu. Rev. Immunol.*, 15:535). These cells are characterized by co-expression of NK cell receptors and semi-invariant T cell receptors (TCR) encoded by Vα14 and Ja281 gene segments in mice and Vα24 and JaQ gene segments in humans. The activation of NKT cells in vivo promptly induces a series of cellular activation events leading to the activation of innate cells such as natural killer (NK) cells and dendritic cells (DC), the activation of adaptive cells such as B cells and T cells, the induction of co-stimulatory molecules and the abrupt release of cytokines such as interleukin-4 (IL-4) and interferon-γ (IFN-γ) (Burdin et al., *Eur. J. Immunol.* 29: 2014-2025, 1999; Carnaud et al., *J. Immunol.*, 163: 4647-4650, 1999; Kitamura et al., *J. Exp. Med.*, 189: 1121-1128, 1999; Kitamura et al., *Cell Immunol.*, 199: 37-42, 2000; Aderem and Ulevitch, *Nature*, 406: 782-787, 2000). In addition, activated NKT cells can themselves bring about killing mediated by Fas and perforin. The full activation cascade can be recruited by the engagement of NKT TCR. Alternatively, powerful T-helper-cell type 1 (Th1) functions can be selectively triggered by cytokines such as interleukin-12 (IL-12) released by infected macrophages or DC. These functions are believed likely to be correlated with the important role of NKT cells in conditions such as autoimmune diabetes, rejection of established tumours or the prevention of chemically induced tumours (Yoshimoto et al., 1995, *Science*, 270: 1845; Hammond et al., *J. Exp. Med.*, 187: 1047-1056, 1998; Kawano et al., 1998, *Proc. Natl. Acad. Sci. USA*, 95: 5690; Lehuen et al., *J. Exp. Med.*, 188: 1831-1839, 1998; Wilson et al., *Nature*, 391: 177-181, 1998; Smyth et al., *J. Exp. Med.*, 191: 661-668, 2000). Finally, NKT cells are thought to contribute to antimicrobial immunity through their capacity to influence the Th1-Th2 polarization (Cui et al., *J. Exp. Med.*, 190: 783-792, 1999; Singh et al., *J. Immunol.*, 163: 2373-2377, 1999; Shinkai and Locksley, *J. Exp. Med.*, 191: 907-914, 2000). These cells are therefore implicated as key effector cells in innate immune responses. However, the potential role of NKT cells in the development of adaptive immune responses remains unclear.

It has been demonstrated that NKT cells can be activated both in vitro and in vivo by α-galactosyl-ceramide (α-GalCer), a glycolipid originally extracted from Okinawan marine sponges (Natori et al., *Tetrahedron*, 50:2771-2784, 1994) or its synthetic analog KRN 7000 [(2S,3 S,4R)-1-0-(α-D-galactopyranosyl)-2-(N-hexacosanoylamino)-1,3,4-octadecan-etriol] which can be obtained from Pharmaceutical Research Laboratories, Kirin Brewery (Gumna, Japan) or synthesized as described previously (see, e.g., Kobayashi et al. 1995, *Onc. Res.* 7:529-534).

Thus, it was shown that α-GalCer can stimulate NK activity and cytokine production by NKT cells and exhibits potent antitumor activity in vivo (Kawano et al., 1997, supra; Kawano et al., 1998, *Proc. Natl. Acad. Sci. USA*, 95:5690; Kitamura et al., 1999, supra). Kitamura et al. (1999, supra) demonstrated that the immunostimulating effect of α-GalCer was initiated by CD40-CD40L-mediated NKT-DC interactions. As the immunoregulatory functions of α-GalCer were absent in both CD1d- and NKT-deficient mice, this indicates that α-GalCer has to be presented by the MHC class I-like molecule CD1d.

CD1 is a conserved family of non-polymorphic genes related to MHC that seems to have evolved to present lipid and glycolipid antigens to T cells and in this way participates in both an innate and an adaptive pathway of antigen recognition (reviewed by Park and Bendelac, *Nature*, 406: 788-792, 2000; see also Calabi et al., *Eur. J. Immunol.*, 19: 285-292, 1989; Porcelli and Modlin, *Annu. Rev. Immunol.*, 17: 297-329, 1999). It comprises up to five distinct genes (isotypes) that can be separated into two groups on the basis of sequence homology. Group 1, which comprises CD1a, CD1b, CD1c and CD1e, is present in humans but absent from mouse and rat. Group 2, which includes CD1d, is found in all species studied so far, including humans.

CD1 isotypes are expressed selectively by antigen-presenting cells such as dendritic cells (DCs), macrophages and subsets of B cells, but apart from CD1d expression in hepatocytes they are generally not expressed in solid tissues (Porcelli et al., supra; Bendelac et al., *Annu. Rev. Immunol.*, 15: 535-562, 1997).

α-GalCer is recognized in picomolar concentrations by those among mouse and human CD1d-restricted lymphocytes that express a semi-invariant TCR and exert potent effector and regulatory functions (Kawano et al., *Science*, 278: 1626-1629, 1997). CD1d/α-GalCer complex is, in turn, recognized by the antigen receptors of mouse Vα14 and human Vα24 natural killer T (NKT) cells (Bendelac et al., Science, 268: 863-865, 1995; Bendelac et al., *Annu. Rev. Immunol.*, 15: 535-562, 1997; Park et al., *Eur. J. Immunol.*, 30: 620-625, 2000).

Upon binding to CD1 d, α-GalCer was demonstrated to activate murine NKT cells both in vivo and in vitro (Kawano et al., 1997, *Science*, 278:1626-1629; Burdin et al., 1998, *J. Immunol.*, 161:3271-3281), and human NKT cells in vitro (Spada et al., 1998, *J. Exp. Med.*, 188:1529-1534; Brossay et al., 1998, *J. Exp. Med.* 188:1521-1528). For example, α-GalCer was shown to display NKT-mediated anti-tumor activity in vitro by activating human NKT cells (Kawano et al., 1999, *Cancer Res.*, 59:5102-5105).

Commonly owned U.S. patent application Ser. No. 10/206, 155, which is hereby incorporated by reference in its entirety, discloses that α-GalCer and related glycosylceramides can be used as adjuvants capable of containing and/or extending the duration of the protective immue responses induced by other anitgens. The '155 application discloses methods and compositions for enhancing and/or extending the duration of the immune response against an antigen in a mammal, notably a human, involving the conjoint immunization of the mammal with (i) an antigen and (ii) an adjuvant.

In contrast to α-GalCer and related glycosylceramides, conventional vaccine delivery systems and the adjuvants approved for human use, aluminium salts and MF59 (Singh and O'Hagan, *Nat. Biotechnol.*, 17: 1075-1081, 1999), are poor at inducing CD8+ T cell responses. Although certain novel adjuvants, such as purified saponins, immunostimulatory complexes, liposomes, CpG DNA motifs, and recombinant attenuated viruses (e.g., adenovirus, Sindbis virus, influenza virus, and vaccinia virus), have been shown to improve the antigen-specific cellular immune responses over those induced by the same antigen given alone or in combination with standard alum adjuvants (Newman et al., *J. Immunol.*, 1992; 148:2357-2362; Takahashi et al., *Nature*, 1990, 344: 873-875; Babu et al., *Vaccine*, 1995, 13:1669-1676; Powers et al., *J. Infect. Dis.*, 1995, 172:1103-7; White et al., *Vaccine*, 1995, 13:1111-1122; Krieg et al., *Trends Microbiol.*, 6: 23-27, 1998; Rodrigues et al., *J. Immunol.*, 158: 1268-1274, 1997; Tsuji et al., *J. Virol.*, 72: 6907-6910, 1998; Li et al., *Proc. Natl. Acad. Sci. USA*, 90: 5214-52188, 1993), none of the currently available adjuvants combine low toxicity in humans, cost-efficiency of production and the ability to efficiently stimulate the immune system.

Commonly owned and copending U.S. patent application Ser. No. 10/462,211, "Synthetic Glycolipid and Its Use for Treating Cancer, Infectious Disease and Autoimmune Disease" discloses a genus of synthetic α-C-galactosylceramides (α-C-GalCer) which display a more potent antimalaria activity than α-GalCer. The '211 application discloses that the compounds are natural killer T cell (NKT cell) ligands, which are useful for treating cancers, autoimmune diseases and infectious diseases.

It has now been found that the α-C-GalCer compounds of the '211 application have utility as adjuvants, by enhancing protective cell-mediated immunity against infectious agents, tumors and autoimmune diseases.

SUMMARY OF THE INVENTION

It is an object of the present invention to provide a method for augmenting the immunogenicity of an antigen in a mammal, comprising administering the antigen conjointly with an adjuvant composition comprising a novel C-glycolipid compound of formula (I)

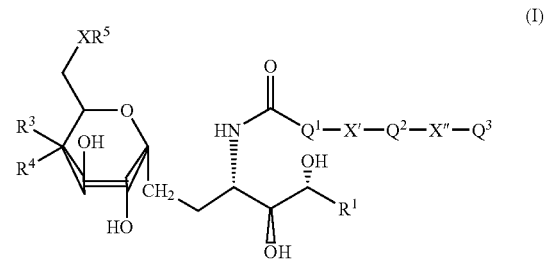

wherein X is O or NH;

$R^1$ is selected from the group consisting of —$(CH_2)_{11}CH_3$, —$(CH_2)_{12}CH_3$, —$(CH_2)_{13}CH_3$, —$(CH_2)_9CH(CH_3)_2$, —$(CH_2)_{10}CH(CH_3)_2$, —$(CH_2)_{11}CH(CH_3)_2$ and $(CH_2)_{11}CH(CH_3)$—$C_2H_5$;

$R^3$ is OH or a monosaccharide and $R^4$ is hydrogen, or $R^3$ is hydrogen and $R^4$ is OH or a monosaccharide;

$R^5$ is hydrogen or a monosaccharide;

$Q^1$ is optionally present and is a $C_{1-10}$ straight or branched chain alkylene, alkenylene, or alkynylene;

X' is optionally present and is O, S or $NR^8$;

$Q^2$ is optionally present and is a $C_{1-10}$ straight or branched chain alkylene, alkenylene or alkynylene;

X" is optionally present and is O, S or $NR^8$;

$Q^3$ is a straight or branched chain $C_{1-10}$ alkyl, alkenyl or alkynyl, or is hydrogen, wherein each $Q^1$, $Q^2$ or $Q^3$ is optionally substituted with hydroxyl, halogen, cyano, nitro, $SO_2$, $NHR^8$, or C(=O)—$R^9$; and wherein $R^8$ is hydrogen, $C_{1-5}$ alkyl, $C_{1-5}$ alkoxy, halogen, cyano, nitro, $SO_2$ or C(=O)—$R^9$;

$R^9$ is hydrogen, $C_{1-5}$ alkyl, $C_{1-5}$ alkoxy or $NHR^{10}$;

$R^{10}$ is hydrogen, $C_{1-5}$ alkyl or $C_{1-5}$ alkoxy;

and pharmaceutically acceptable salts or esters thereof.

The monosaccharide groups may be attached to the $R^3$, $R^4$ or $R^5$ structure, to form a glycosyl bond. Typically, the monosaccharide is attached to the $R^3$, $R^4$ or $R^5$ position at the oxygen attached to the C-1 carbon of the monosaccharide, forming the standard glycoside linkage.

According to the present invention, the use of the glycolipid compounds of formula I as an adjuvant results in an enhancement and/or extension of the duration of the protective immunity induced by the antigen and is attributed at least in part to the enhancement and/or extension of antigen-specific Th1-type responses, in particular, CD8+ T cell responses.

The adjuvant of the invention comprising a glycolipid compound of formula I can be conjointly administered with any antigen, in particular, with antigens derived from infectious agents or tumors. Preferably, the adjuvant and antigen are administered simultaneously, most preferably in a single dosage form.

In a further embodiment, the invention provides a prophylactic and/or therapeutic method for treating a disease in a mammal comprising administering to said mammal an immunoprotective antigen together with an adjuvant composition that includes a compound of formula I. As specified herein, this method can be useful for preventing and/or treating various infectious, neoplastic or autoimmune diseases. In a preferred embodiment, the method of the invention is employed to treat an infection selected from the group consisting of viral infection, bacterial infection, parasitic infection, and fungal infection.

Thus, in a specific embodiment, the present invention discloses a method for conferring immunity against the sporozoite stage of malaria in a mammal (e.g., human), wherein said method comprises conjointly administering to said mammal a malaria-specific antigen and an immunoadjuvant comprising a compound of formula I. In another specific embodiment, the invention discloses a method for enhancing the immune response to HIV infection (and potentially preventing and/or treating AIDS) in a mammal, wherein said method comprises conjointly administering to said mammal an HIV-specific antigen and an adjuvant comprising a compound of formula I. Additional specific methods disclosed herein include without limitation:

(i) enhancing the immune response to *Mycobacterium bovis* Bacillus Calmette-Guérin for prevention of *M. tuberculosis* infection, by administering *Mycobacterium bovis Bacillus* Calmette-Guerin and an adjuvant comprising a compound of formula I;

(ii) enhancing the immune response to melanoma by administering a plasmid cDNA coding for the human melanoma-associated antigen, gp 100, and an adjuvant comprising a compound of formula I;

(iii) enhancing the immune response to *Candida albicans* by administering peptides derived from the immunodominant antigen, 65 kDa mannoprotein (MP65) and an adjuvant comprising a compound of formula I.

In conjunction with the methods of the present invention, also provided are pharmaceutical and vaccine compositions comprising an immunogenically effective amount of an antigen and an immunogenically effective amount of an adjuvant of a compound of Formula I as well as a pharmaceutically acceptable carrier or excipient.

The antigens useful in the compositions of the present invention include without limitation various viral, bacterial, fungal, parasite-specific, and tumor-specific antigens. Non-limiting examples of viral antigens of the invention include HIV antigens such as gp120, gp 160, p18, Tat, Gag, Pol, Env, Nef; glycoprotein from Herpesvirus; surface antigen and core antigen from Hepatitis B virus. Non-limiting examples of bacterial antigens of the invention include OspA, OspB and OspC antigens from *Borrelia* sp. Non-limiting examples of fungal and parasite antigens of the invention include MP65 from *Candida albicans* and CS protein from *Plasmodium* sp., respectively. Non-limiting examples of tumor-specific antigens of the invention include Melan A and gp 100 antigens from melanoma.

In a specific embodiment, the antigen is malaria-specific and comprises, for example, irradiated plasmodial sporozoites or a synthetic peptide antigen comprising a T cell epitope of the malarial circumsporozoite (CS) protein such as CD4+ T cell epitope YNRNIVNR LLGDALNGKPEEK (SEQ ID NO: 1) or CD8+ T cell epitope SYVPSAEQI (SEQ ID NO: 2) of *P. yoelii* CS protein, or CD4+ T cell epitope $(NVDPNANP)_n$ (SEQ ID NO: 3), or CD4+/CD8+ T cell epitope EYLNKIQNSLSTEWSPCSVT (SEQ ID NO: 4) of *P. falciparum* CS protein. In another preferred embodiment, the antigen is HIV-specific such as CD8+ T cell epitope RGPGRAFVTI (SEQ ID NO: 5) of p18 protein or HIV-1 Gag p24 CD8+ T cell epitopes (e.g., KAFSPEVIPMF (aa 30-40, SEQ ID NO: 6), KAFSPEVI (aa 30-37, SEQ ID NO: 7), TPQDLNM (or T) ML (aa 180-188, SEQ ID NOS: 8 and 9), DTINEEAAEW (aa 203-212, SEQ ID NO: 10), KRWIILGLNK (aa 263-272, SEQ ID NO: 11), and QATQEVKNW (aa 308-316, SEQ ID NO: 12)), or Gag p17 CD8+ T cell epitopes (e.g., RLRPGGKKK (aa 20-29, SEQ ID NO: 13) and SLYNTVATL (aa 77-85, SEQ ID NO: 14)).

In a specific embodiment, the antigen is presented by a recombinant virus expressing said antigen. Preferably, the virus is selected from the group consisting of a recombinant adenovirus, recombinant pox virus, and recombinant Sindbis virus.

In another embodiment, the invention is directed to a method for preparing a vaccine composition comprising at least one antigen and an adjuvant compound of formula I, said method comprising admixing the adjuvant and the antigen.

In another embodiment, the invention is directed to a kit for the preparation of a pharmaceutical or vaccine composition comprising at least one antigen and an adjuvant compound of formula I, said kit comprising the antigen in a first container, and the adjuvant in a second container, and optionally instructions for admixing the antigen and the adjuvant and/or for administration of the composition; and wherein optionally the containers are in a package.

A preferred compound of formula (I) is 3'S,4'S,5'R-3'-hexacosanoyl-4,5'-di-O-acetylnonadecyl-2,3,4,6-tetra-O-acetyl-α-C-D-galactopyranoside (wherein X is O, $R^3$ is OH, $R^4$ and $R^5$ are hydrogen, $R^1$ is $—(CH_2)_{13}CH_3$, $Q^1$ is $C_{25}$ alkenyl, $X^1$, $Q^2$ and X" are absent, and $Q^3$ is hydrogen), which is depicted below:

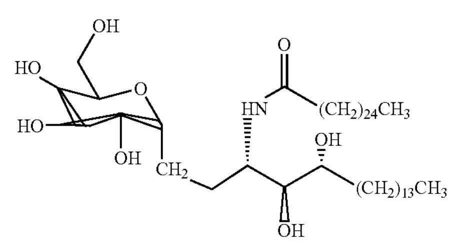

The preferred compound is also known as CRONY-101.

DESCRIPTION OF THE DRAWINGS

FIG. 1 depicts the adjuvant effects of α-GalCer on DNA vaccination in mice, and the enhancement of HIV-specific CD4+/CD8+ T-Cell responses;

FIG. 2 depicts the adjuvant activity of CRONY 101, and the enhancement of a malaria-specific CD8+ T-cell response elicited by a recombinant adenovirus expressing a malaria antigen; and FIGS. 3A and 3B depict the adjuvant activity of α-GalCer and CRONY 101, and the enhancement of a Gag-specific CD8+ T-cell response elicited by a DNA vaccine encoding an HIV-Gag sequence.

DETAILED DESCRIPTION OF THE INVENTION

As reported in copending U.S. patent application Ser. No. 10/206,155, α-Galactosylceramide (α-GalCer) is a glycolipid ligand for natural killer T (NKT) cells, which respond to the glycolipid and produce both interferon (IFN)-γ and interleukin (IL)-4. The production of large amounts of both cytokines, which possess opposite biological effects, i.e. Th1- and Th2-type response, hampers α-GalCer from executing either desired effect. It has now been discovered that synthetic C-glycoside analogs of α-GalCer of general formula (I) act as an NKT cell ligand and display 100-1000 fold higher activity against tumor and malaria, by preferentially inducing the production of Th1-type cytokines, IFN-γ and IL-12, in vivo. Administration of the α-C-GalCer to mice consistently resulted in not only prolonged production of the Th1-type cytokines, but also decreased population of the Th2 cytokine, IL-4, as compared to α-GalCer. In two disease models requiring Th1-type responses for control, namely malaria and melanoma metastases, α-C-GalCer exhibited a 1000-fold and 100-fold more potent activity, respectively, than α-GalCer.

DEFINITIONS

The term "monosaccharide" means a sugar molecule having a chain of 3-10 carbon atoms in the form of an aldehyde (aldose) or ketone (ketose). Suitable monosaccharides contemplated for use in the invention include both naturally occuring and synthetic monosaccharides. Sample monosaccharides include trioses, such as glycerose and dihydroxyacetone; textroses such as erythrose and erythrulose; pentoses such as xylose, arabinose, ribose, xylulose ribulose; methyl pentoses (6-deoxyhexoses), such as rhamnose and fucose; hexoses, such as glucose, mannose, galactose, fructose and sorbose; and heptoses, such as glucoheptose, galamannoheptose, sedoheptulose and mannoheptulose. Preferred monosaccharides are hexoses.

The terms "adjuvant" and "immunoadjuvant" are used interchangeably in the present invention and refer to a compound or mixture that may be non-immunogenic when administered to a host alone, but that augments the host's immue response to another antigen when administered cojointly with that antigen.

Adjuvant-mediated enhancement and/or extension of the duration of the immune response can be assessed by any method known in the art including without limitation one or more of the following: (i) an increase in the number of antibodies produced in response to immunization with the adjuvant/antigen combination versus those produced in response to immunization with the antigen alone; (ii) an increase in the number of T cells recognizing the antigen or the adjuvant; and (iii) an increase in the level of one or more Type I cytokines.

The adjuvant of the invention can be administered as part of a pharmaceutical or vaccine composition comprising an antigen or as a separate formulation, which is administered conjointly with a second composition containing an antigen. In any of these compositions the compounds of the invention can be combined with other adjuvants and/or excipients/carriers. These other adjuvants include, but are not limited to, oil-emulsion and emulsifier-based adjuvants such as complete Freund's adjuvant, incomplete Freund's adjuvant, MF59, or SAF; mineral gels such as aluminum hydroxide (alum), aluminum phosphate or calcium phosphate; microbially-derived adjuvants such as cholera toxin (CT), pertussis toxin, *Escherichia coli* heat-labile toxin (LT), mutant toxins (e.g., LTK63 or LTR72), Bacille Calmette-Guerin (BCG), *Corynebacterium parvum*, DNA CpG motifs, muramyl dipeptide, or monophosphoryl lipid A; particulate adjuvants such as immunostimulatory complexes (ISCOMs), liposomes, biodegradable microspheres, or saponins (e.g., QS-21); cytokines such as IFN-γ, IL-2, IL-12 or GM-CSF; synthetic adjuvants such as nonionic block copolymers, muramyl peptide analogues (e.g., N-acetyl-muramyl-L-threonyl-D-isoglutamine [thr-MDP], N-acetyl-nor-muramyl-L-alanyl-D-isoglutamine, N-acetylmuramyl-L-alanyl-D-isoglutaminyl-L-alanine-2-[1'-2'-dipalmitoyl-sn-glycero-3-hydroxyphosphoryloxy]-ethylamine), polyphosphazenes, or synthetic polynucleotides, and surface active substances such as lysolecithin, pluronic polyols, polyanions, peptides, hydrocarbon emulsions, or keyhole limpet hemocyanins (KLH). Preferably, these additional adjuvants are also pharmaceutically acceptable for use in humans.

As used herein, the term "conjoint administration" means administration of an immune adjuvant and an antigen simultaneously in one composition, or simultaneously in different compositions, or sequentially. For the sequential administration to be considered "conjoint," however, the antigen and adjuvant must be administered separated by a time interval that still permits the adjuvant to augment the immune response to the antigen. For example, when the antigen is a polypeptide, the antigen and adjuvant are administered on the same day, preferably within an hour of each other, and most preferably simultaneously. However, when nucleic acid is delivered to the subject and the polypeptide antigen is expressed in the subject's cells, the adjuvant is administered within 24 hours of nucleic acid administration, preferably within 6 hours.

As used herein, the term "immunogenic" means that an agent is capable of eliciting a humoral or cellular immune response, and preferably both. An immunogenic entity is also antigenic. An immunogenic composition is a composition that elicits a humoral or cellular immune response, or both, when administered to an animal having an immune system.

The term "antigen" refers to any agent (e.g., protein, peptide, polysaccharide, glycoprotein, glycolipid, nucleic acid, or combination thereof) that, when introduced into a host, animal or human, having an immune system (directly or upon expression as in, e.g., DNA vaccines), is recognized by the immune system of the host and is capable of eliciting an immune response. As defined herein, the antigen-induced immune response can be humoral or cell-mediated, or both. An agent is termed "antigenic" when it is capable of specifically interacting with an antigen recognition molecule of the immune system, such as an immunoglobulin (antibody) or T cell antigen receptor (TCR). Within the meaning of the present invention, the antigens are preferably "surface antigens", i.e., expressed naturally on the surface of a pathogen, or the surface of an infected cell, or the surface of a tumor cell. A molecule that is antigenic need not be itself immunogenic, i.e., capable of eliciting an immune response without an adjuvant or carrier.

The term "epitope" or "antigenic determinant" refers to any portion of an antigen recognized either by B cells, or T cells, or both. Preferably, interaction of such epitope with an antigen recognition site of an immunoglobulin (antibody) or T cell antigen receptor (TCR) leads to the induction of antigen-specific immune response. T cells recognize proteins only when they have been cleaved into smaller peptides and are presented in a complex called the "major histocompatability complex (MHC)" located on another cell's surface. There are two classes of MHC complexes-class I and class II, and each class is made up of many different alleles. Class I MHC complexes are found on virtually every cell and present peptides from proteins produced inside the cell. Thus, class I MHC complexes are useful for killing cells infected by viruses or cells which have become cancerous as the result of expression of an oncogene. T cells which have a protein called CD8 on their surface, bind specifically to the MHC class I/peptide complexes via the T cell receptor (TCR). This leads to cytolytic effector activities. Class II MHC complexes are found only on antigen-presenting cells (APC) and are used to present peptides from circulating pathogens which have been endocytosed by APCs. T cells which have a protein called CD4 bind to the MHC class II/peptide complexes via TCR. This leads to the synthesis of specific cytokines which stimulate an immune response. To be effectively recognized by the immune system via MHC class I presentation, an antigenic polypeptide has to contain an epitope of at least about 8 to 10 amino acids, while to be effectively recognized by the immune system via MHC class II presentation, an antigenic polypeptide has to contain an epitope of at least about 13 to 25 amino acids. See, e.g., *Fundamental Immunology*, 3rd Edition, W. E. Paul ed., 1999, Lippincott-Raven Publ.

The term "species-specific" antigen refers to an antigen that is only present in or derived from a particular species. Thus, the term "malaria-derived" or "malaria-specific" antigen refers to a natural (e.g., irradiated sporozoites) or synthetic (e.g., chemically produced multiple antigen peptide [MAP] or recombinantly synthesized polypeptide) antigen comprising at least one epitope (B cell and/or T cell) derived from any one of the proteins constituting *plasmodium* (said *plasmodium* being without limitation *P. falciparum, P. vivax, P. malariae, P. ovale, P. reichenowi, P. knowlesi, P. cynomolgi, P. brasilianum, P. yoelii, P. berghei*, or *P. chabaudi*) and comprising at least 5-10 amino acid residues. A preferred plasmodial protein for antigen generation is circumsporozoite (CS) protein, however, other proteins can be also used, e.g., Thrombospondin Related Adhesion (Anonymous) protein (TRAP), also called Sporozoite Surface Protein 2 (SSP2), LSA-1, hsp70, SALSA, STARP, Hep17, MSA, RAP-1, RAP-2, etc.

The term "vaccine" refers to a composition (e.g., protein or vector such as, e.g., an adenoviral vector, Sindbis virus vector, or pox virus vector) that can be used to elicit protective immunity in a recipient. It should be noted that to be effective, a vaccine of the invention can elicit immunity in a portion of the immunized population, as some individuals may fail to mount a robust or protective immune response, or, in some cases, any immune response. This inability may stem from the individual's genetic background or because of an immunodeficiency condition (either acquired or congenital) or immunosuppression (e.g., due to treatment with chemotherapy or use of immunosuppressive drugs, e.g., to prevent organ rejection or suppress an autoimmune condition). Vaccine efficacy can be established in animal models.

The term "DNA vaccine" is an informal term of art, and is used herein to refer to a vaccine delivered by means of a recombinant vector. An alternative, and more descriptive term used herein is "vector vaccine" (since some potential vectors, such as retroviruses and lentiviruses are RNA viruses, and since in some instances non-viral RNA instead of DNA is delivered to cells through the vector). Generally, the vector is administered in vivo, but ex vivo transduction of appropriate antigen presenting cells, such as dendritic cells (DC), with administration of the transduced cells in vivo, is also contemplated.

The term "treat" is used herein to mean to relieve or alleviate at least one symptom of a disease in a subject. Within the meaning of the present invention, the term "treat" may also mean to prolong the prepatency, i.e., the period between infection and clinical manifestation of a disease. Preferably, the disease is either infectious disease (e.g., viral, bacterial, parasitic, or fungal) malignancy (e.g., solid or blood tumors such as sarcomas, carcinomas, gliomas, blastomas, pancreatic cancer, breast cancer, ovarian cancer, prostate cancer, lymphoma, leukemia, melanoma, etc.), or an autoimmune disease.

The term "protect" is used herein to mean prevent or treat, or both, as appropriate, development or continuance of a disease in a subject. Within the meaning of the present invention, the disease is selected from the group consisting of infection (e.g., viral, bacterial, parasitic, or fungal) and malignancy (e.g., solid or blood tumors such as sarcomas, carcinomas, gliomas, blastomas, pancreatic cancer, breast cancer, ovarian cancer, prostate cancer, lymphoma, leukemia, melanoma, etc.). For example, as disclosed herein, a prophylactic administration of an anti-malarial vaccine comprising a plasmodium-derived antigen in combination with an adjuvant comprising a compound of the invention can protect a recipient subject at risk of developing malaria. Similarly, according to the present invention, a therapeutic administration of a tumor-specific antigen conjointly with an adjuvant comprising a compound of the invention of Formula I can enhance an anti-tumor immune response leading to slow-down in tumor growth and metastasis or even tumor regression.

The term "protective immunity" refers to an immune response in a host animal (either active/acquired or passive/innate, or both) which leads to inactivation and/or reduction in the load of said antigen and to generation of long-lasting immunity (that is acquired, e.g., through production of antibodies), which prevents or delays the development of a disease upon repeated exposure to the same or a related antigen. A "protective immune response" comprises a humoral (antibody) immunity or cellular immunity, or both, effective to, e.g., eliminate or reduce the load of a pathogen or infected cell (or produce any other measurable alleviation of the infection), or to reduce a tumor burden in an immunized (vaccinated) subject. Within the meaning of the present invention, protective immunity may be partial.

Immune systems are classified into two general systems, the "innate" or "natural" immune system and the "acquired" or "adaptive" immune system. It is thought that the innate immune system initially keeps the infection under control, allowing time for the adaptive immune system to develop an appropriate response. Recent studies have suggested that the various components of the innate immune system trigger and augment the components of the adaptive immune system, including antigen-specific B and T lymphocytes (Fearon and Locksley, supra; Kos, 1998, *Immunol. Res.*, 17: 303; Romagnani, 1992, *Immunol. Today*, 13: 379; Banchereau and Steinman, 1988, *Nature*, 392: 245).

The term "innate immunity" or "natural immunity" refers to innate immune responses that are not affected by prior contact with the antigen. Cells of the innate immune system, including macrophages and dendritic cells (DC), take up foreign antigens through pattern recognition receptors, combine peptide fragments of these antigens with MHC class I and class II molecules, and stimulate naive CD8+ and CD4+ T cells respectively (Banchereau and Steinman, supra; Holmskov et al, 1994, *Immunol. Today*, 15: 67; Ulevitch and Tobias, 1995, *Annu. Rev. Immunol.*, 13: 437). Professional antigen-presenting cells (APC) communicate with these T cells leading to the differentiation of naive CD4+ T cells into T-helper 1 (Th1) or T-helper 2 (Th2) lymphocytes that mediate cellular and humoral immunity, respectively (Trinchieri, 1995, *Annu. Rev. Immunol.*, 13: 251; Howard and O'Garra, 1992, *Immunol. Today*, 13: 198; Abbas et al., 1996, *Nature*, 383: 787;

Okamura et al., 1998, *Adv. Immunol.*, 70: 281; Mosmann and Sad, 1996, Immunol. Today, 17: 138; O'Garra, 1998, *Immunity*, 8: 275).

The term "acquired immunity" or "adaptive immunity" is used herein to mean active or passive, humoral or cellular immunity that is established during the life of an animal, is specific for the inducing antigen, and is marked by an enhanced response on repeated encounters with said antigen. A key feature of the T lymphocytes of the adaptive immune system is their ability to detect minute concentrations of pathogen-derived peptides presented by MHC molecules on the cell surface.

As used herein, the term "augment the immune response" means enhancing or extending the duration of the immune response, or both. When referred to a property of an agent (e.g., adjuvant), the term "[able to] augment the immunogenicity" refers to the ability to enhance the immunogenicity of an antigen or the ability to extend the duration of the immune response to an antigen, or both.

As used herein, the phrase "enhance immune response" refers to the property or process of increasing the scale and/or efficiency of immunoreactivity to a given antigen, said immunoreactivity being either humoral or cellular immunity, or both. An immune response is believed to be enhanced if any measurable parameter of antigen-specific immunoreactivity (e.g., antibody titer, T cell production) is increased at least two-fold, preferably ten-fold, most preferably thirty-fold.

The term "therapeutically effective" applied to dose or amount refers to that quantity of a compound or pharmaceutical composition or vaccine that is sufficient to result in a desired activity upon administration to a mammal in need thereof. As used herein with respect to adjuvant- and antigen-containing compositions or vaccines, the term "therapeutically effective amount/dose" is used interchangeably with the term "immunogenically effective amount/dose" and refers to the amount/dose of a compound (e.g., an antigen and/or an adjuvant comprising a compound of the invention) or pharmaceutical composition or vaccine that is sufficient to produce an effective immune response upon administration to a mammal.

The phrase "pharmaceutically acceptable," as used in connection with compositions of the invention, refers to molecular entities and other ingredients of such compositions that are physiologically tolerable and do not typically produce untoward reactions (such as gastric upset, dizziness and the like) when administered to a human. Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the term "pharmaceutically acceptable salts, esters, amides, and prodrugs" refers to those salts (e.g., carboxylate salts, amino acid addition salts), esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention.

The term "carrier" applied to pharmaceutical or vaccine compositions of the invention refers to a diluent, excipient, or vehicle with which a compound (e.g., an antigen and/or an adjuvant comprising a compound of the invention) is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution, saline solutions, and aqueous dextrose and glycerol solutions are preferably employed as carriers, particularly for injectable solutions. Suitable pharmaceutical carriers are described in "Remington's Pharmaceutical Sciences" by E. W. Martin, 18th Edition.

The term "native antibodies" or "immunoglobulins" refers to usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain (VL) at one end and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., *J. Mol. Biol.*, 186: 651-663, 1985; Novotny and Haber, *Proc. Natl. Acad. Sci. USA*, 82: 4592-4596, 1985).

The term "antibody" or "Ab" is used in the broadest sense and specifically covers not only native antibodies but also single monoclonal antibodies (including agonist and antagonist antibodies), antibody compositions with polyepitopic specificity, as well as antibody fragments (e.g., Fab, F(ab')2, scFv and Fv), so long as they exhibit the desired biological activity.

"Cytokine" is a generic term for a group of proteins released by one cell population which act on another cell population as intercellular mediators. Examples of such cytokines are lymphokines, monokines, and traditional polypeptide hormones. Included among the cytokines are interferons (IFN, notably IFN-γ), interleukins (IL, notably IL-1, IL-2, IL-4, IL-10, IL-12), colony stimulating factors (CSF), thrombopoietin (TPO), erythropoietin (EPO), leukemia inhibitory factor (LIF), kit-ligand, growth hormones (GH), insulin-like growth factors (IGF), parathyroid hormone, thyroxine, insulin, relaxin, follicle stimulating hormone (FSH), thyroid stimulating hormone (TSH), leutinizing hormone (LH), hematopoietic growth factor, hepatic growth factor, fibroblast growth factors (FGF), prolactin, placental lactogen, tumor necrosis factors (TNF), mullerian-inhibiting substance, mouse gonadotropin-associated peptide, inhibin, activin, vascular endothelial growth factor (VEGF), integrin, nerve growth factors (NGF), platelet growth factor, transforming growth factors (TGF), osteoinductive factors, etc.

The term "subject" as used herein refers to an animal having an immune system, preferably a mammal (e.g., rodent such as mouse). In particular, the term refers to humans.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

Where particular values are described in the application and claims, unless otherwise stated the term "about" meaning within an acceptable error range for the particular value should be assumed.

The terms "vector", "cloning vector", and "expression vector" mean the vehicle by which a DNA or RNA sequence (e.g., a foreign gene) can be introduced into a host cell, so as to transform the host and promote expression (e.g., transcription and/or translation) of the introduced sequence. Vectors include plasmids, phages, viruses, etc.

A "nucleic acid molecule" (or alternatively "nucleic acid") refers to the phosphate ester polymeric form of ribonucleosides (adenosine, guanosine, uridine, or cytidine: "RNA molecules") or deoxyribonucleosides (deoxyadenosine, deoxyguanosine, deoxythymidine, or deoxycytidine: "DNA molecules"), or any phosphoester analogs thereof, such as phosphorothioates and thioesters, in either single stranded form, or a double-stranded helix. Oligonucleotides (having fewer than 100 nucleotide constituent units) or polynucleotides are included within the defined term as well as double stranded DNA-DNA, DNA-RNA, and RNA-RNA helices. This term, for instance, includes double-stranded DNA found, inter alia, in linear (e.g., restriction fragments) or circular DNA molecules, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

As used herein, the term "polypeptide" refers to an amino acid-based polymer, which can be encoded by a nucleic acid or prepared synthetically. Polypeptides can be proteins, protein fragments, chimeric proteins, etc. Generally, the term "protein" refers to a polypeptide expressed endogenously in a cell. Generally, a DNA sequence encoding a particular protein or enzyme is "transcribed" into a corresponding sequence of mRNA. The mRNA sequence is, in turn, "translated" into the sequence of amino acids which form a protein. An "amino acid sequence" is any chain of two or more amino acids. The term "peptide" is usually used for amino acid-based polymers having fewer than 100 amino acid constituent units, whereas the term "polypeptide" is reserved for polymers having at least 100 such units. Herein, however, "polypeptide" will be the generic term.

In accordance with the present invention there may be employed conventional molecular biology, microbiology, and recombinant DNA techniques within the skill of the art. Such techniques are well-known and are explained fully in the literature. See, e.g., Sambrook, Fritsch and Maniatis, *Molecular Cloning: A Laboratory Manual*, Second Edition (1989) Cold Spring Harbor Laboratory Press, Cold Spring Harbor, N.Y. (herein "Sambrook et al., 1989"); DNA *Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therapeutic Uses for Adjuvants of the Invention

In one aspect, the present invention provides a method for augmenting the immunogenicity of an antigen in a mammal, comprising administering said antigen conjointly with an adjuvant composition comprising a glycolipid compound of Formula I, preferably CRONY 101. According to the present invention, the use of compounds of Formula I as an adjuvant results in an enhancement and/or extension of the duration of the protective immunity induced by the antigen. For example, as disclosed herein, conjoint administration of compounds of formula I with peptides corresponding to T cell or B cell epitopes of tumor or viral antigens, or DNA constructs expressing these antigens enhances antigen-specific immune responses.

The adjuvants of Formula I can be conjointly administered with any antigen, in particular, with antigens derived from infectious agents or tumors.

As discussed in the Background Section, the immunostimulating effects of the compounds of formula I both in mice and humans depend on the expression of CD1d molecules and are mediated by NKT cells. Indeed, the instant invention demonstrates that the adjuvant activity of the Formula I compound is attributed at least in part to the ability to enhance and/or extend NKT-mediated antigen-specific Th1-type T cell responses and CD8+ T cell (or Tc) responses.

From an immunotherapy view point, activation of the NKT cell system by the compounds of Formula I appear to have distinct advantages over the other mechanisms for the following reasons: (a) the level of cytotoxicity of activated NKT cells is very high and effective against a wide variety of tumor cells or infected cells; (b) the activation of NKT cells by the Formula I compounds is totally dependent on a CD1d molecule, which is monomorphic among individuals (Porcelli, *Adv. Immunol.*, 59: 1-98, 1995), indicating that adjuvants of the invention can be utilized by all patients, regardless of MHC haplotype; (c) antigen-presenting functions of DC and NKT activation of human patients can be evaluated before immunotherapy by the in vivo assays in mice using Vα14 NKT cell status as an indicator.

According to the present invention, an adjuvant comprising compounds of Formula I and antigen can be administered either as two separate formulations or as part of the same composition. If administered separately, the adjuvant and antigen can be administered either sequentially or simultaneously. As disclosed herein, simultaneous administration of a Formula I compound adjuvant with the antigen is preferred and generally permits the most efficient immunostimulation.

As the adjuvant of the invention exerts its immunostimulatory activity in combination with a plurality of different antigens, it is therefore useful for both preventive and therapeutic applications. Accordingly, in a further aspect, the invention provides a prophylactic and/or therapeutic method for treating a disease in a mammal comprising conjointly administering to said mammal an antigen and an adjuvant comprising a compound of Formula I. This method can be useful, e.g., for protecting against and/or treating various infections as well as for treating various neoplastic diseases.

Immunogenicity enhancing methods of the invention can be used to combat infections, which include, but are not limited to, parasitic infections (such as those caused by plasmodial species, etc.), viral infections (such as those caused by influenza viruses, leukemia viruses, immunodeficiency viruses such as HIV, papilloma viruses, herpes virus, hepatitis viruses, measles virus, poxviruses, mumps virus, cytomegalovirus [CMV], Epstein-Barr virus, etc.), bacterial infections (such as those caused by staphylococcus, streptococcus, pneumococcus, *Neisseria gonorrhea, Borrelia, pseudomonas*, etc.), and fungal infections (such as those caused by candida, trichophyton, ptyrosporum, etc.).

As further disclosed herein, maximal efficiency of the immunogenicity enhancing methods of present invention is attained when an antigen and an adjuvant for Formula I are administered simultaneously.

In a specific embodiment, the present invention discloses a method for preventing and/or treating malaria in a mammal (e.g., human), wherein said method comprises conjointly administering to said mammal a malaria-specific antigen and an adjuvant comprising a compound of Formula I, preferably CRONY 101. Co-administration with a compound of Formula I not only increases the level of protection but also prolongs the duration of protective anti-malaria immunity. Furthermore, it is disclosed herein that co-injection of mice with a compound of Formula I and irradiated parasites or peptides (corresponding to CD4+ or CD8+ epitopes of the malarial CS protein), leads to an increase in the number of antigen-specific T cells.

In another specific embodiment, the invention discloses a method for enhancing the immune response to HIV infection (and potentially preventing and/or treating AIDS) in a mammal, wherein said method comprises conjointly administering to said mammal an HIV-specific antigen and an adjuvant compound of Formula I.

The methods of the invention can be used in conjunction with other treatments. For example, an anti-cancer treatment using tumor-specific antigen and containing an adjuvant of the present invention can be used in combination with chemotherapy and/or radiotherapy and/or IL-12 treatment. Antiviral vaccines comprising adjuvants of the invention can be used in combination with IFN-α treatment.

In addition to the therapeutic applications, the adjuvants of the invention may be also applied as a research tool to the study of many aspects of basic immunology. For example, the adjuvants can be used to study immune mechanisms, such as function of NKT cells, antigen presentation by DC, and modulation of immune responses by cytokines and their receptors. The adjuvants of the invention can be also employed in vaccine design research, which could assist in identifying the requirements for protective immunity, since for the same antigen different adjuvants may produce immune responses of varying intensity and/or length.

More specifically, the compounds of this invention are useful in the treatment of a variety of cancers including, but not limited to carcinoma such as bladder, breast, colon, kidney, liver, lung, including small cell lung cancer, non-small cell lung cancer, esophagus, gall bladder, ovary, pancreas, testicular, stomach, renal, liver, cervix, thyroid, prostate, and skin, including squamous cell carcinoma; hematopoietic tumors of lymphoid lineage, including leukemia, acute lymphocitic leukemia, acute lymphoblastic leukemia, B cell lymphoma, T cell lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xenoderoma pigmentosum, keratoctanthoma, thyroid follicular cancer and Kaposi's sarcoma.

Cell proliferative disorders for which the compounds are useful include benign prostate hyperplasia, familial adenomatosis polyposis, neuro fibromatosis, psoriasis, vascular smooth cell proliferation associated with atherosclerosis, pulmonary fibrosis, arthritis glomerulonephritis and post-surgical stenosis and restenosis.

In another embodiment, the compounds of the invention are also useful for treating infectious diseases, including parasitic, fungal, yeast, bacterial, mycoplasmal and viral diseases (where a particular class of cells can be identified as harboring the infective entity).

For example, the compounds may be useful in treating infections from a human papilloma virus, a herpes virus such as herpes simplex or herpes zoster, a retrovirus such as human immunodeficiency virus 1 or 2, a hepatitis virus (hepatitis A virus (HAV)), hepatitis B virus (HBV) non-A, blood borne (hepatitis C) and other enterically transmitted hepatitis (hepatitis E), and HBV associated delta agent (hepatitis D)), influenza virus, rhinovirus, respiratory syncytial virus, cytomegalovirus, adenovirus, *Mycoplasma pneumoniae*, a bacterium of the genus *Salmonella, Staphylococcus, Streptococcus, Enterococcus, Clostridium, Escherichia, Klebsiella, Vibrio, Mycobacterium*, amoeba, a malarial parasite, *Trypanosoma cruzi*, helminth infections, such as nematodes (round worms) (*Trichuriasis, Enterobiasis, Ascariasis*, Hookworm, *Strongyloidiasis, Trichinosis, filariasis*); trematodes (flukes) (*Schistosomiasis, Clonorchiasis*), cestodes (tape worms) (*Echinococcosis, Taeniasis saginata, Cysticercosis*); visceral worms, visceral larva migrans (e.g., *Toxocara*), eosinophilic gastroenteritis (e.g., *Anisaki* spp., *Phocanema* ssp.), cutaneous larva migrans (*Ancylostona braziliense, Ancylostoma caninum*).

In certain preferred embodiments, the compounds of the invention are useful for treating infection with a hepatitis C virus.

In other preferred embodiments, the compounds of the invention are useful for treating human immunodeficiency virus (HIV), and in the prevention of infection by HIV, the treatment of infection by HIV and the prevention and/or treatment of the resulting acquired immune deficiency syndrome (AIDS).

In another preferred embodiment, the compounds of the invention are useful for treating malaria in a mammal (e.g., human) by administration of a compound of the invention.

The subjects to which the present invention is applicable may be any mammalian or vertebrate species, which include, but are not limited to, cows, horses, sheep, pigs, fowl (e.g., chickens), goats, cats, dogs, hamsters, mice, rats, monkeys, rabbits, chimpanzees, and humans. In a preferred embodiment, the subject is a human.

Pharmaceutical and Vaccine Compositions

In conjunction with the method of the present invention, also provided are pharmaceutical and vaccine compositions comprising an immunogenically effective amount of an antigen and immunogenically effective amount of an adjuvant comprising a compound of Formula I and, optimally, an additional immunostimulant, carrier or excipient (preferably all pharmaceutically acceptable). Said antigen and adjuvant can be either formulated as a single composition or as two separate compositions, which can be administered simultaneously or sequentially.

The antigens used in immunogenic (e.g., vaccine) compositions of the instant invention can be derived from a eukaryotic cell (e.g., tumor, parasite, fungus), bacterial cell, viral particle, or any portion thereof. In the event the material to which the immunogenic response is to be directed is poorly antigenic, it may be additionally conjugated to a carrier molecule such as albumin or hapten, using standard covalent binding techniques, for example, with one of the several commercially available reagent kits.

Examples of preferred antigens of the present invention include (i) malaria-specific antigens such as irradiated plasmodial sporozoites or synthetic peptide antigens comprising at least one T cell and/or B cell epitope of the malarial circumsporozoite (CS) protein (see below); (ii) viral protein or peptide antigens such as those derived from influenza virus (e.g., surface glycoproteins hemagluttinin (HA) and neuraminidase (NA) [such as turkey influenza HA or an avian influenza A/Jalisco/95H5 HA); immunodeficiency virus (e.g., a feline immunodeficiency virus (FIV) antigen, a simian immunodeficiency virus (SIV) antigen, or a human immunodeficiency virus antigen (HIV) such as gp120, gp 160, p18 antigen, Gag p17/p24, Tat, Pol, Nef, and Env; herpesvirus (e.g., a glycoprotein, for instance, from feline herpesvirus, equine herpesvirus, bovine herpesvirus, pseudorabies virus, canine herpesvirus, herpes simplex virus (HSV, e.g., HSV tk, gB, gD), Marek's Disease Virus, herpesvirus of turkeys (HVT), or cytomegalovirus (CMV), or Epstein-Barr virus); hepatitis virus (e.g., Hepatitis B surface antigen (HBsAg)); papilloma virus; bovine leukemia virus (e.g., gp51,30 envelope antigen); feline leukemia virus (FeLV) (e.g., FeLV envelope protein, a Newcastle Disease Virus (NDV) antigen, e.g., HN or F); rous associated virus (such as RAV-1 env); infectious bronchitis virus (e.g., matrix and/or preplomer); flavivirus (e.g., a Japanese encephalitis virus (JEV) antigen, a Yellow Fever antigen, or a Dengue virus antigen); Morbillivirus (e.g., a canine distemper virus antigen, a measles antigen, or rinderpest antigen such as HA or F); rabies (e.g., rabies glycoprotein G); parvovirus (e.g., a canine parvovirus antigen); poxvirus (e.g., an ectromelia antigen, a canary poxvirus antigen, or a fowl poxvirus antigen); chicken pox virus (varicella zoster antigen); infectious bursal disease virus (e.g., VP2, VP3, or VP4); Hantaan virus; mumps virus; (iii) bacterial antigens such as lipopolysaccharides isolated from gram-negative bacterial cell walls and *staphylococcus*-specific, *streptococcus*-specific, pneumococcus-specific (e.g., PspA [see PCT Publication No. WO 92/14488]), *Neisseria gonorrhea*-specific *Borrelia*-specific (e.g., OspA, OspB, OspC antigens of *Borrelia* associated with Lyme disease such as *Borrelia burgdorferi, Borrelia afzelli*, and *Borrelia garinii* [see, e.g., U.S. Pat. No. 5,523,089; PCT Publication Nos. WO 90/04411, WO 91/09870, WO 93/04175, WO 96/06165, WO93/08306; PCT/US92/08697; Bergstrom et al., *Mol. Microbiol.,* 3: 479-486, 1989; Johnson et al., *Infect. and Immun.* 60: 1845-1853, 1992; Johnson et al., Vaccine 13: 1086-1094, 1995; *The Sixth International Conference on Lyme Borreliosis: Progress on the Development of Lyme Disease Vaccine, Vaccine* 13: 133-135, 1995]), and pseudomonas-specific proteins or peptides; (iv) fungal antigens such as those isolated from candida, trichophyton, or ptyrosporum, and (v) tumor-specific proteins such as ErbB receptors, Melan A [MARTI], gp100, tyrosinase, TRP-1/gp 75, and TRP-2 (in melanoma); MAGE-1 and MAGE-3 (in bladder, head and neck, and non-small cell carcinoma); HPV EG and E7 proteins (in cervical cancer); Mucin [MUC-1] (in breast, pancreas, colon, and prostate cancers); prostate-specific antigen [PSA] (in prostate cancer); carcinoembryonic antigen [CEA] (in colon, breast, and gastrointestinal cancers) and such shared tumor-specific antigens as MAGE-2, MAGE-4, MAGE-6, MAGE-10, MAGE-12, BAGE-1, CAGE-1,2,8, CAGE-3 to 7, LAGE-1, NY-ESO-1/LAGE-2, NA-88, GnTV, and TRP2—INT2.

The foregoing list of antigens are intended as exemplary, as the antigen of interest can be derived from any animal or human pathogen or tumor. With respect to DNA encoding pathogen-derived antigens of interest, attention is directed to, e.g., U.S. Pat. Nos. 4,722,848; 5,174,993; 5,338,683; 5,494, 807; 5,503,834; 5,505,941; 5,514,375; 5,529,780; U.K. Patent No. GB 2 269 820 B; and PCT Publication Nos. WO 92/22641; WO 93/03145; WO 94/16716; WO 96/3941; PCT/US94/06652. With respect to antigens derived from tumor viruses, reference is also made to Molecular Biology of Tumor Viruses, RNA Tumor Viruses, Second Edition, Edited by Weiss et al., Cold Spring Harbor Laboratory Press, 1982. For a list of additional antigens useful in the compositions of the invention see also Stedman's Medical Dictionary (24th edition, 1982).

In a specific embodiment, the compositions of the present invention provide protective immunity against malaria, in particular against *P. yoelii* and major human plasmodial species *P. falciparum* and *P. vivax*. These compositions comprise one or more of the following components: (i) at least one malaria-specific peptide comprising a T cell epitope capable of eliciting an anti-malarial T-cell response preferably in mammals of diverse genetic backgrounds (e.g., YNRNIVN-RLLGDALNGKPEEK [SEQ ID NO: 1] or SYVPSAEQI [SEQ ID NO: 2] T cell epitope of *P. yoelii* CS protein [Renia et al., *J. Immunol.,* 22: 157-160, 1993; Rodrigues et al., *Int. Immunol.,* 3: 579-585, 1991] or (NVDPNANP)$_n$ [SEQ ID NO: 3] or EYLNKIQNSLSTE WSPCSVT [SEQ ID NO: 4] T cell epitope of *P. falciparum* CS protein [Nardin et al., *Science* 246:1603, 1989; Moreno et al., *Int. Immunol.* 3: 997, 1991; Moreno et al., *J. Immunol.* 151: 489, 1993]); (ii) at least one malaria-specific peptide comprising a B cell epitope (e.g., (NANP)$_3$ [SEQ ID NO: 15] B cell epitope located within the repeat region of the CS protein of *P. falciparum* [Nardin et al., *J. Exp. Med.* 156: 20, 1982; Nardin et al., *Ann. Rev. Immunol.* 11: 687, 1993]) capable of stimulating the production of anti-malarial (i.e., neutralizing) antibodies (e.g., directed against the sporozoite stage of the malarial organism). Preferably, the immunogenic compositions of the present invention comprise at least one B cell epitope and at least one T cell epitope. B cell epitopes preferably elicit the production of antibodies that specifically recognize and bind to the malarial circumsporozoite (CS) protein. Alternatively or in addition, the compositions of the invention may comprise B cell and/or T cell epitopes derived from, and reactive with, other malarial components, such as, for example, the *P. vivax* Erythrocyte Secreted Protein-1 or -2 (PvESP-1 or PvESP-2) (see, e.g., U.S. Pat. No. 5,874,527), *P. falciparum* sporozoite surface protein designated Thrombospondin Related Adhesion (Anonymous) protein (TRAP), also called Sporozoite Surface Protein 2 (SSP2), LSA-1, hsp70, SALSA, STARP, Hep17, MSA, RAP-1, and RAP-2. In one embodiment, the B cell epitope and T cell epitope components are incorporated into multiple antigen peptides (MAPs), forming a synthetic macromolecular polypeptide containing a high density of the epitopes. Methods for MAP synthesis are well known in the art (see, e.g., Tam, *Proc. Natl. Acad. Sci. USA,* 85: 5409, 1988; Tam, *Meth. Enzymol.,* 168: 7, 1989).

The present invention also encompasses B cell and T cell epitopes derived from other plasmodial species, including without limitation *P. malariae, P. ovale, P. reichenowi, P. knowlesi, P. cynomolgi, P. brasilianum, P. berghei*, and *P. chabaudi*. These epitopes typically comprise between 8 and 18 amino acid residues, derived from a plasmodial protein.

In another specific embodiment, a preferred antigen of the invention is HIV-specific (such as T cell epitope RGPGRAFVTI [SEQ ID NO: 5] of p18 protein, see Example 2, infra). As disclosed herein, compositions comprising such HIV-specific antigen(s) and an adjuvant comprising a compound of Formula I, preferably CRONY 101, are capable of enhancing a T cell response to an HIV antigen in a susceptible mammalian host.

In yet another specific embodiment, an antigen of the invention is influenza A virus-specific. As disclosed herein, co-administration of a compound of Formula I with a suboptimal dose ($10^5$ p.f.u.) of a recombinant Sindbis virus expressing a CD8+ T cell epitope TYQRTRALV (SEQ ID NO: 16) of the nucleoprotein (NP) of the influenza A virus (Tsuji et al., *J. Virol.*, 72:6907-6910, 1998) significantly enhances the CD8+ T cell anti-influenza response in a susceptible mammalian host.

To provide additional antigen-derived B and T cell epitopes for use in the compositions of the present invention, these epitopes may be identified by one or a combination of several methods well known in the art, such as, for example, by (i) fragmenting the antigen of interest into overlapping peptides using proteolytic enzymes, followed by testing the ability of individual peptides to bind to an antibody elicited by the full-length antigen or to induce T cell or B cell activation (see, e.g., Janis Kuby, *Immunology*, pp. 79-80, W. H. Freeman, 1992); (ii) preparing synthetic peptides whose sequences are segments or analogs of a given antigen (see, e.g., Alexander et al., 1994, *Immunity*, 1:751-61; Hammer et al., 1994, *J. Exp. Med.*, 180:2353-8), or constructs based on such segments, or analogs linked or fused to a carrier or a heterologous antigen and testing the ability of such synthetic peptides to elicit antigen-specific antibodies or T cell activation (e.g., testing their ability to interact with MHC class II molecules both in vitro and in vivo [see, e.g., O'Sullivan et al., 1991, *J. Immunol.*, 147:2663-9; Hill et al., 1991, *J. Immunol.*, 147:189-197]); for determination of T cell epitopes, peptides should be at least 8 to 10 amino acids long to occupy the groove of the MHC class I molecule and at least 13 to 25 amino acids long to occupy the groove of MHC class II molecule, preferably, the peptides should be longer; these peptides should also contain an appropriate anchor motif which will enable them to bind to various class I or class II MHC molecules with high enough affinity and specificity to generate an immune response (see Bocchia et al., *Blood* 85: 2680-2684, 1995; Englehard, *Ann. Rev. Immunol.* 12: 181, 1994); (iii) sequencing peptides associated with purified MHC molecules (see, e.g., Nelson et al., 1997, PNAS, 94:628-33); (iv) screening a peptide display library for high-affinity binding to MHC class II molecules, TCR, antibodies raised against a full-length antigen, etc. (see, e.g., Hammer et al., 1992, *J. Exp. Med.*, 176:1007-13); (v) computationally analyzing different protein sequences to identify, e.g., hydrophilic stretches (hydrophilic amino acid residues are often located on the surface of the protein and are therefore accessible to the antibodies) and/or high-affinity TCR or MHC class II allele-specific motifs, e.g., by comparing the sequence of the protein of interest with published structures of peptides associated with the MHC molecules (Mallios, *Bioinformatics*, 15:432-439, 1999; Milik et al., *Nat. Biotechnol.*, 16:753-756, 1998; Brusic et al., *Nuc. Acids Res*, 26:368-371, 1998; Feller and de la Cruz, *Nature*, 349:720-721, 1991); (vi) performing an X-ray crystallographic analysis of the native antigen-antibody complex (Janis Kuby, *Immunology*, p. 80, W. H. Freeman, 1992), and (vii) generating monoclonal antibodies to various portions of the antigen of interest, and then ascertaining whether those antibodies attenuate in vitro or in vivo growth of the pathogen or tumor from which the antigen was derived (see U.S. Pat. No. 5,019,384 and references cited therein).

In a specific embodiment, the antigen of the invention may be presented by a recombinant virus expressing said antigen. Preferably, the virus is selected from the group consisting of a recombinant adenovirus, recombinant pox virus, and recombinant Sindbis virus.

In the disclosed compositions, both the antigen and the adjuvant of the invention are present in immunogenically effective amounts. For each specific antigen, the optimal immunogenically effective amount should be determined experimentally (taking into consideration specific characteristics of a given patient and/or type of treatment). Generally, this amount is in the range of 0.1 μg-100 mg of an antigen per kg of the body weight. For the adjuvant of Formula I the present invention, the optimal immunogenically effective amount is preferably in the range of 10-100 μg of the adjuvant per kg of the body weight.

The invention also provides a method for preparing a vaccine composition comprising at least one antigen and an adjuvant comprising a compound of Formula I, preferably CRONY 101, said method comprising admixing the adjuvant and the antigen, and optionally one or more physiologically acceptable carriers and/or excipients and/or auxiliary substances.

Formulations and Administration

The invention provides pharmaceutical and vaccine formulations containing therapeutics of the invention (an antigen and adjuvant compound of Formula I either as a single composition or as two separate compositions which can be administered simultaneously or sequentially), which formulations are suitable for administration to elicit an antigen-specific protective immune response for the treatment and prevention of infectious or neoplastic diseases described above. Compositions of the present invention can be formulated in any conventional manner using one or more physiologically acceptable carriers or excipients. Thus, an antigen and/or an adjuvant comprising a compound of Formula 1, preferably CRONY 101, can be formulated for administration by transdermal delivery, or by transmucosal administration, including but not limited to, oral, buccal, intranasal, opthalmic, vaginal, rectal, intracerebral, intradermal, intramuscular, intraperitoneal, intravenous, subcutaneous routes, via scarification (scratching through the top layers of skin, e.g., using a bifurcated needle), by inhalation (pulmonary) or insufflation (either through the mouth or the nose), or by administration to antigen presenting cells ex vivo followed by administration of the cells to the subject, or by any other standard route of immunization.

Preferably, the immunogenic formulations of the invention can be delivered parenterally, i.e., by intravenous (i.v.), subcutaneous (s.c.), intraperitoneal (i.p.), intramuscular (i.m.), subdermal (s.d.), or intradermal (i.d.) administration, by direct injection, via, for example, bolus injection, continuous infusion, or gene gun (e.g., to administer a vector vaccine to a subject, such as naked DNA or RNA). Formulations for injection can be presented in unit dosage form, e.g., in ampoules or in multi-dose containers, with an added preservative. The compositions can take such forms as excipients, suspensions, solutions or emulsions in oily or aqueous vehicles, and can contain formulatory agents such as suspending, stabilizing and/or dispersing agents. Alternatively, the active ingredient can be in powder form for reconstitution with a suitable vehicle, e.g., sterile pyrogen-free water, before use.

The present invention also contemplates various mucosal vaccination strategies. While the mucosa can be targeted by local delivery of a vaccine, various strategies have been employed to deliver immunogenic compositions to the mucosa. For example, in a specific embodiment, the immunogenic polypeptide or vector vaccine can be administered in an admixture with, or as a conjugate or chimeric fusion protein with, cholera toxin, such as cholera toxin B or a cholera toxin A/B chimera (see, e.g., Hajishengallis, *J. Immunol.*, 154: 4322-32, 1995; Jobling and Holmes, *Infect Immun.*, 60: 4915-24, 1992; Lebens and Holmgren, *Dev Biol Stand* 82: 215-27, 1994). In another embodiment, an admixture with heat labile enterotoxin (LT) can be prepared for mucosal vaccination. Other mucosal immunization strategies include encapsulating the immunogen in microcapsules (see, e.g., U.S. Pat. Nos. 5,075,109; 5,820,883, and 5,853,763) and using an immunopotentiating membranous carrier (see, e.g., PCT Application No. WO 98/0558). Immunogenicity of orally administered immunogens can be enhanced by using red blood cells (rbc) or rbc ghosts (see, e.g., U.S. Pat. No. 5,643,577), or by using blue tongue antigen (see, e.g., U.S. Pat. No. 5,690,938). Systemic administration of a targeted immunogen can also produce mucosal immunization (see, U.S. Pat. No. 5,518,725). Various strategies can be also used to deliver genes for expression in mucosal tissues, such as using chimeric rhinoviruses (see, e.g., U.S. Pat. No. 5,714, 374), adenoviruses, vaccinia viruses, or specific targeting of a nucleic acid (see, e.g., PCT Application No. WO 97/05267).

For oral administration, the formulations of the invention can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. The compositions of the invention can be also introduced in microspheres or microcapsules, e.g., fabricated from poly-glycolic acid/lactic acid (PGLA) (see, U.S. Pat. Nos. 5,814,344; 5,100,669 and 4,849,222; PCT Publication Nos. WO 95/11010 and WO 93/07861). Liquid preparations for oral administration can take the form of, for example, solutions, syrups, emulsions or suspensions, or they can be presented as a dry product for reconstitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound.

For administration by inhalation, the therapeutics according to the present invention can be conveniently delivered in the form of an aerosol spray presentation from pressurized packs or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insulator can be formulated containing a powder mix of the compound and a suitable powder base such as lactose or starch.

Compositions of the present invention can also be formulated in rectal compositions such as suppositories or retention enemas, e.g., containing conventional suppository bases such as cocoa butter or other glycerides.

In addition to the formulations described previously, the compositions can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

As disclosed herein, an antigen and/or adjuvant compound of Formula I can be mixed with excipients which are pharmaceutically acceptable and compatible with the active ingredients. Suitable excipients are, for example, water, saline, buffered saline, dextrose, glycerol, ethanol, sterile isotonic aqueous buffer or the like and combinations thereof. In addition, if desired, the preparations may also include minor amounts of auxiliary substances such as wetting or emulsifying agents, pH buffering agents, and/or immune stimulators (e.g., adjuvants in addition to a compound of Formula I) that enhance the effectiveness of the pharmaceutical composition or vaccine. Non-limiting examples of additional immune stimulators which may enhance the effectiveness of the compositions of the present invention include immunostimulatory, immunopotentiating, or pro-inflammatory cytokines, lymphokines, or chemokines or nucleic acids encoding them (specific examples include interleukin (IL)-1, IL-2, IL-3, IL-4, IL-12, IL-13, granulocyte-macrophage (GM)-colony stimulating factor (CSF) and other colony stimulating factors, macrophage inflammatory factor, Flt3 ligand, see additional examples of immunostimulatory cytokines in the Section entitled "Definitions"). These additional immunostimulatory molecules can be delivered systemically or locally as proteins or by expression of a vector that codes for expression of the molecule. The techniques described above for delivery of the antigen and an adjuvant compound of Formula I can also be employed for the delivery of additional immunostimulatory molecules.

The invention also provides a pharmaceutical pack or kit comprising one or more containers filled with one or more of the ingredients of the immunogenic formulations of the invention. In a related embodiment, the present invention provides a kit for the preparation of a pharmaceutical or vaccine composition comprising at least one antigen and an adjuvant compound of Formula I, said kit comprising the antigen in a first container, and the adjuvant in a second container, and optionally instructions for admixing the antigen and the adjuvant and/or for administration of the composition. Each container of the kit may also optionally include one or more physiologically acceptable carriers and/or excipients and/or auxiliary substances. Associated with such container(s) can be a notice in the form prescribed by a governmental agency regulating the manufacture, use or sale of pharmaceuticals or biological products, which notice reflects approval by the agency of manufacture, use or sale for human administration.

The compositions may, if desired, be presented in a pack or dispenser device which may contain one or more unit dosage forms containing the active ingredient (i.e., an antigen and/or a an adjuvant compound of Formula I). The pack may, for example, comprise metal or plastic foil, such as a blister pack. The pack or dispenser device may be accompanied by instructions for administration. Compositions of the invention formulated in a compatible pharmaceutical carrier may also be prepared, placed in an appropriate container, and labeled for treatment of an indicated condition.

Effective Dose and Safety Evaluations

According to the methods of the present invention, the pharmaceutical and vaccine compositions described herein are administered to a patient at immunogenically effective doses, preferably, with minimal toxicity. As recited in the Section entitled "Definitions", "immunogenically effective dose" or "therapeutically effective dose" of disclosed formulations refers to that amount of an antigen and/or adjuvant compound of Formula I that is sufficient to produce an effective immune response in the treated subject and therefore sufficient to result in a healthful benefit to said subject.

Following methodologies which are well-established in the art (see, e.g., reports on evaluation of several vaccine formulations containing novel adjuvants in a collaborative effort between the Center for Biological Evaluation and Food and Drug Administration and the National Institute of Allergy and Infectious Diseases [Goldenthal et al., National Cooperative Vaccine Development Working Group. AIDS Res. Hum. Retroviruses, 1993, 9:545-9]), effective doses and toxicity of the compounds and compositions of the instant invention are first determined in preclinical studies using small animal models (e.g., mice) in which both the antigen and adjuvant compound of Formula I has been found to be immunogenic and that can be reproducibly immunized by the same route proposed for the human clinical trials. Specifically, for any pharmaceutical composition or vaccine used in the methods of the invention, the therapeutically effective dose can be estimated initially from animal models to achieve a circulating plasma concentration range that includes the $IC_{50}$ (i.e., the concentration of the test compound which achieves a half-maximal inhibition of symptoms). Dose-response curves derived from animal systems are then used to determine testing doses for the initial clinical studies in humans. In safety determinations for each composition, the dose and frequency of immunization should meet or exceed those anticipated for use in the clinical trial.

As disclosed herein, the dose of the adjuvant of Formula I, antigen(s) and other components in the compositions of the present invention is determined to ensure that the dose administered continuously or intermittently will not exceed a certain amount in consideration of the results in test animals and the individual conditions of a patient. A specific dose naturally varies depending on the dosage procedure, the conditions of a patient or a subject animal such as age, body weight, sex, sensitivity, feed, dosage period, drugs used in combination, seriousness of the disease. The appropriate dose and dosage times under certain conditions can be determined by the test based on the above-described indices and should be decided according to the judgment of the practitioner and each patient's circumstances according to standard clinical techniques. In this connection, the dose of an antigen is generally in the range of 0.1 μg-100 mg per kg of body weight, and the dose of the adjuvant compound of Formula I required for augmenting the immune response to the antigen is generally in the range of 10-100 μg per kg of the body weight.

Toxicity and therapeutic efficacy of immunogenic compositions of the invention containing a compound of Formula I can be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferred. While therapeutics that exhibit toxic side effects can be used (e.g., when treating severe forms of cancer or life-threatening infections), care should be taken to design a delivery system that targets such immunogenic compositions to the specific site (e.g., lymphoid tissue mediating an immune response, tumor or an organ supporting replication of the infectious agent) in order to minimize potential damage to other tissues and organs and, thereby, reduce side effects. As disclosed herein (see also Background Section and Examples), the adjuvant compounds of Formula I of the invention are not only highly immunostimulating at relatively low doses (e.g., 10-100 μg of the adjuvant per kg of the body weight) but also possesses low toxicity and do not produce significant side effects.

As specified above, the data obtained from the animal studies can be used in formulating a range of dosage for use in humans. The therapeutically effective dosage of compositions of the present invention containing a compound of Formula I in humans lies preferably within a range of circulating concentrations that include the $ED_{50}$ with little or no toxicity. The dosage can vary within this range depending upon the dosage form employed and the route of administration utilized. Ideally, a single dose should be used.

Synthesis of Adjuvant Compounds of Formula I

The compounds of formula I, and the methods of synthesizing the compounds, is disclosed in commonly owned co-pending application Ser. No. 10/462,211, which is hereby incorporated by reference in its entirety. For example, the compounds of the invention may be generally formed by synthesis from commercially available starting materials galactose penta acetate (1) and L-homoserine (2), as shown below:

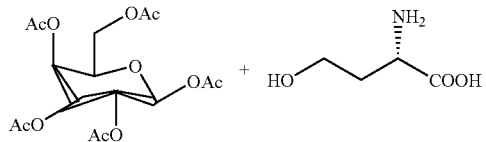

As taught by Kolb et al, 1994, Chem. Rev. 94: 2483, hydroxy groups are introduced into the homosphingosine moiety. As taught in Belica, et al, 1998, Tetrahedron Lett. 39: 8225-8228, Yang et al., 1999, Organic Letters 1: 2149-2151, and Yang, et al, 2001, Organic Letters 3: 197-200, the homosphingosine is linked to the galactose. The alpha configuration is established using the method of Yang, et al., 1999, Organic Letters 1: 2149-2151. The sphingosine is converted to the ceramide using well-established methods.

The compounds of formula (I) may be formed by acylating the compound of formula (II) with a reactant $R^x$—C(=O)-Q'X'Q$^2$X"Q$^3$ to add the C(=O)-Q$^1$X'Q$^2$X"Q$^3$ chain at the amino nitrogen position of (II). The acylation of an amino group is well known to chemists skilled in the art of organic synthesis. Suitable reactants include p-nitrophenyl carboxylates, wherein $R^x$ is p-nitrophenyl as taught in Morita et al. J. Med. Chem, 1995, 38: 2176-2187. Alternative $R^x$ groups include o-nitrophenyl, o-N-succinimidyl, chloride, bromide, or mixed anhydrides.

Compounds of formula (I) wherein X is NH may be formed according to the methods taught by Savage et al., Org. Lett. 2002 Apr. 18 4(8): 1267-70.

Exemplary Embodiments of the Invention

The compounds of this invention and their preparation can be understood further by the examples which illustrate some of the processes by which these compounds are prepared or used. Theses examples do not limit the invention. Variations of the invention, now known or further developed, are considered to fall within the scope of the present invention as hereinafter claimed.

1. Synthesis of CRONY-101

The α-GalCer derivative CRONY-101 may be synthesized according to the following synthesis.

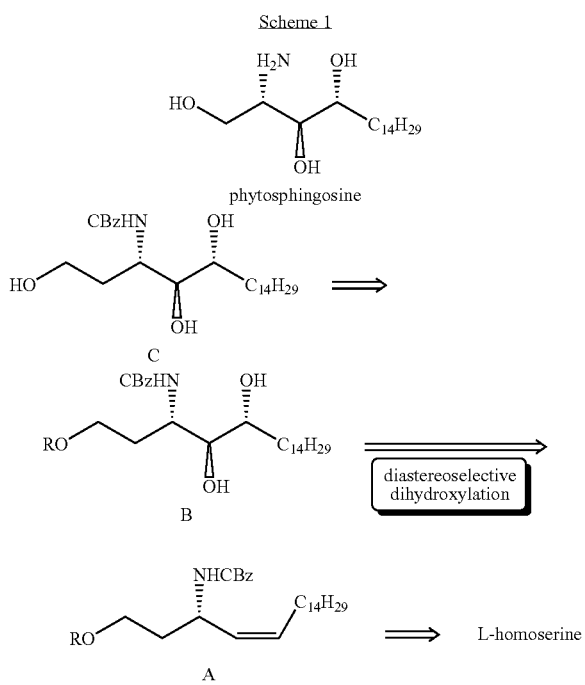

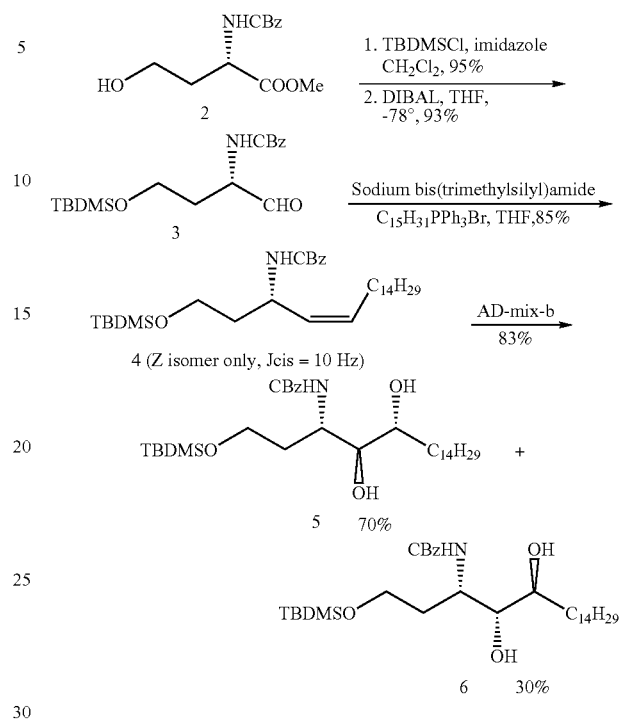

The diastereoselective dihydroxylation of the optically active olefin A, which is readily accessible from L-homoserine, would afford the protected homophytosphingosine derivative B in a stereoselective fashion. The synthetic route from commercially available L-homoserine is shown in Scheme 2.

L-homoserine 1 was converted into methyl ester 2 via two steps in 60% overall yield (Ozinskas, A. et al., *J. Org. Chem.* 1986, 51, 5047-5050; Shioiri, T. et al., *Org. Synth.,* 1989, 68, 1). After the primary alcohol was protected, the ester was reduced to an aldehyde 3 using diisobutylaluminum hydride (DIBAL) as the reducing reagent. The aldehyde was then coupled to $C_{15}$ long-chain Wittig phosphonium salt using sodium hexamethyldisilazane (NaHMDS) in THF(−75° C.) to give Z-olefin 4 as the only product (Beaulieu, P. L. et al., *Org. Chem.* 1991, 56, 4196-4204; Imashiro, R. et al, *Tetrahedron* 1998, 54, 10657-10670). Sharpless dihydroxylation (Sharpless, K. B. et al., *J. Org. Chem.* 1992, 57, 2768-2771), of the optically active Z-olefin using AD-mix-β gave ca. 7:3 mixture of 3S, 4S, 5R (5) and 3S, 4R, 5S (6) dihydroxylated isomers, respectively. Their relative and absolute configurations were confirmed by comparison of NMR data of their cyclic carbamate derivatives.

Scheme 2

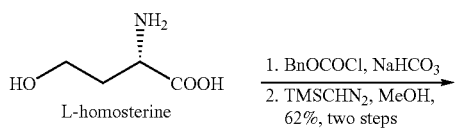

Acetonide formation was used to protect the 1,2-diols in compound 5 (Scheme 3), then the primary alcohol 8 was released by desilylation of 7. Because the basic fluoride ion caused the cyclization, acetic acid was added to $Bu_4NF$ solution as the buffer (Niu, C. et al., *J. Org. Chem.* 1996, 61, 1014-1022) to afford 8 as the only product, since there was no cyclic compound formed. The iodo compound 9 can be made easily by using $PPh_3$, iodine and imidazole reflux in THF (Spak, S. J. et al., Tetrahedron 2000, 56, 217-224).

Based on the general idea of synthesis of the model α-C-galactoside (Yang, G. et al., *Org. Lett.;* 1999, 1, 2149-2151), the synthesis was continued by treatment of thioacetate 10 with hydrazinium acetate in DMF under $N_2$ to deprotect thioacetate (Park, W. K. C. et al., *Carbohydr. Lett.* 1995, 1, 179-184). The freshly deprotected thio derivative was subsequently treated with electrophile 9 to provide thio-galactoside 11 in 95% overall yield (Scheme 4). Treatment of β-D-thiogalactoside 11 with NaOMe in MeOH followed by protection using p-methoxybenzaldehyde.

Scheme 3

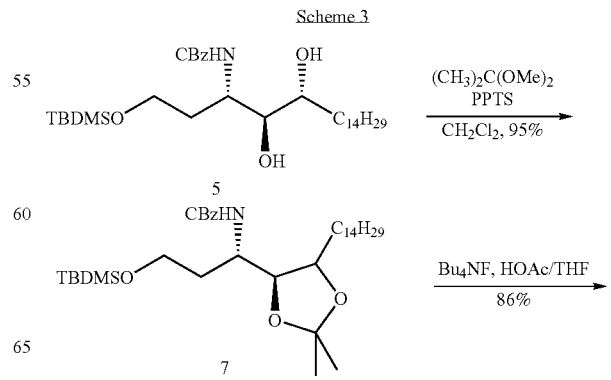

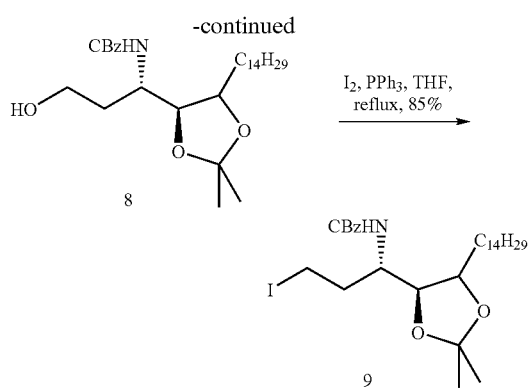

Dimethyl acetal (Johansson, R. et al., J. Chem. Soc. Perkin-Trans. 1 1984, 2371-2374) and p-toluene sulfonic acid gave 4,6-O-(4-methoxybenzylidene)-β-D-1-thio-galactoside 12 in 86% yield. Benzylation of 12 followed by oxidation of thiogalactoside using MMPP gave sulfonyl galactoside 13 in good yield. N-benzlyation could not be avoided in this step.

The RB reaction using $C_2F_4Br_2$/t-BuOH at reflux afforded the product 14 (Scheme 5). The ratio of Z:E alkene isomers was not determined because of peak broadening in the NMR. The intermediate 1-O-Methyl-2,3-dibenzyl β-galactoside can be made in one step by using chlorotrimethylsilane in methanol. Esterification of the primary hydroxyl group at C6 afforded the benzoate 15 in 88% yield (Scheme 5). Treatment of the acetonide 15 with 1N HCl/$Et_2O$ in methanol generated the corresponding diol 16. Cyclic carbonation of the diol using triphosgene (Burk, R. M. et al., Tetrahedron Lett. 1993, 34, 395-398) followed by silylation of the axial hydroxyl group at C4 afforded the silyl ether 17. Pump additon (Mc-Combie, S. W. et al., Tetrahedron Lett. 1991, 32, 2083-2086) of 17 in $CH_2Cl_2$ (0.01M) to $BF_3$. $Et_2O$ in $CH_2Cl_2$ solution (4:1, 0.05M) afford α-C-galactoside 18 and cyclized compound 19(20%). Treatment of silyl ether 18 with 1N $Bu_4NF$ in THF afforded product 20, which is identified by $^1H$ NMR (anomeric H: 3.95 ppm, $J_{12}$=4.6 Hz) and TLC.

Scheme 4

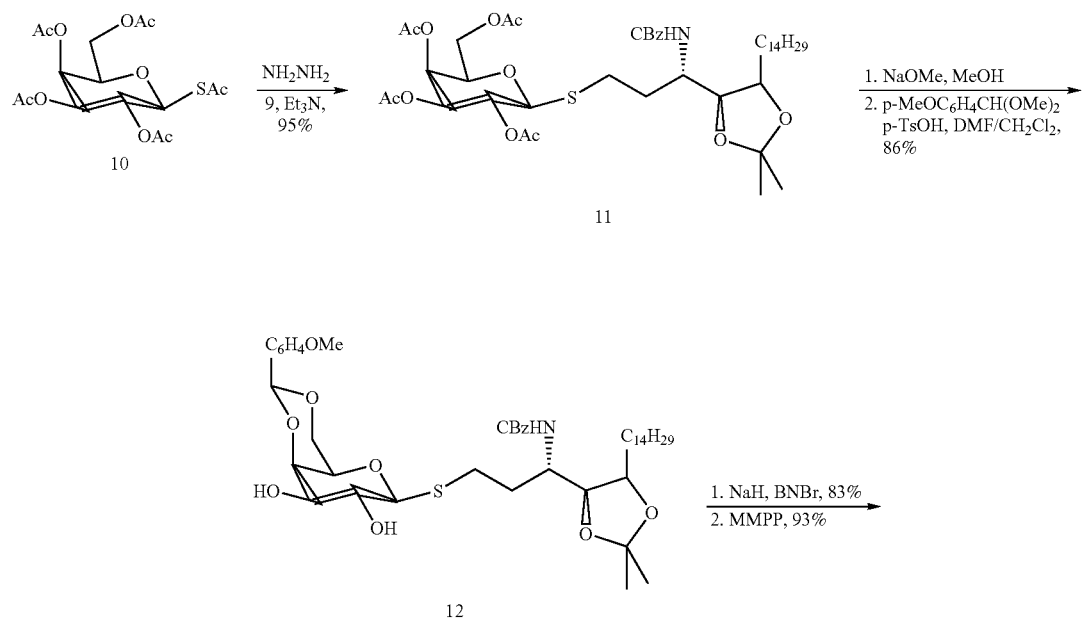

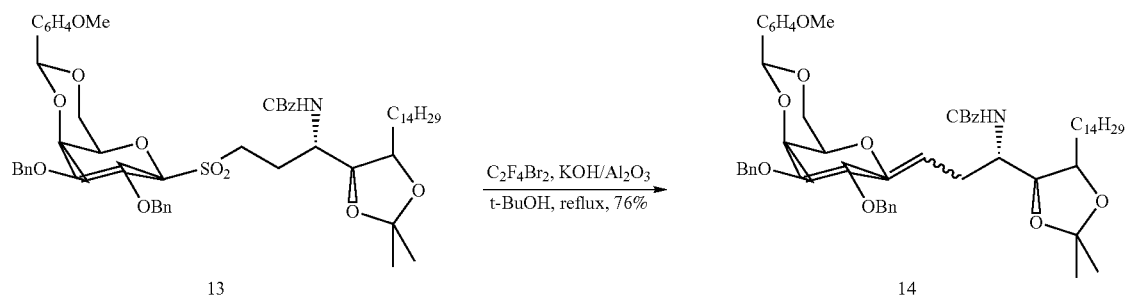

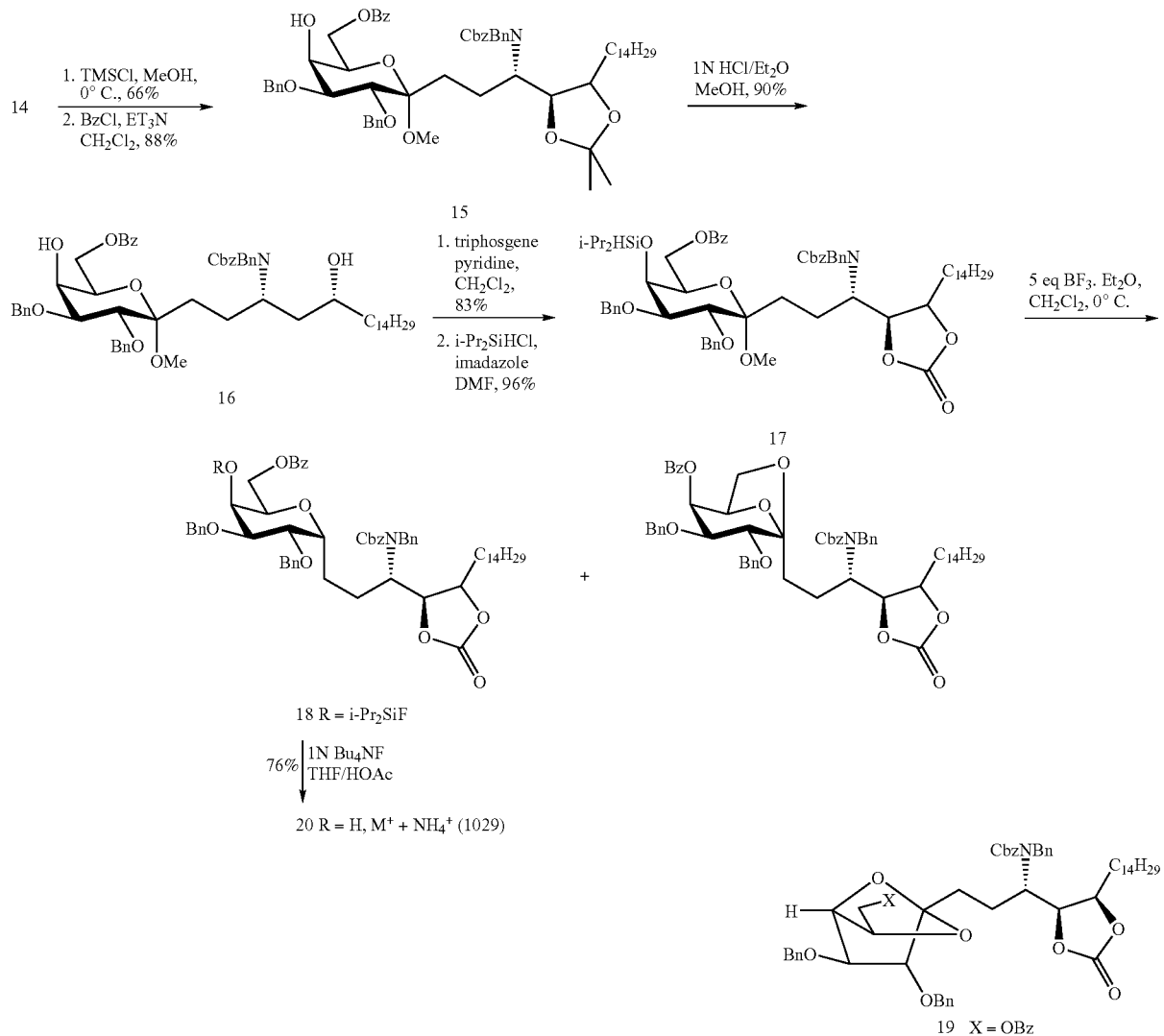
The carbonyl groups were removed prior to debenzylation. Compound 20 was treated with NaOH and refluxed in 1:1 dioxane and H$_2$O to afford the oxazolidinone 21 (Scheme 6). Hydrolysis of 21 gave the N-benzylamine 22, which was fully debenzylated by transfer hydrogenolysis (10% Pd/C, cyclohexene) (Roush, W. R. et al., J. Org. Chem. 1985, 50, 3752-3757) to afford crude 23 in 80% overall yield. The fatty
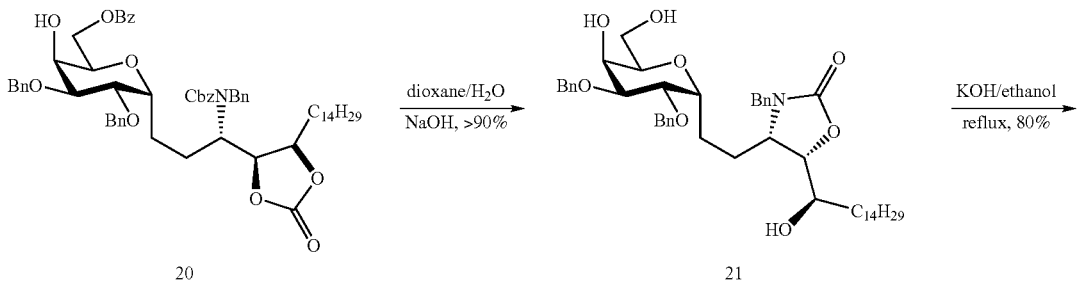

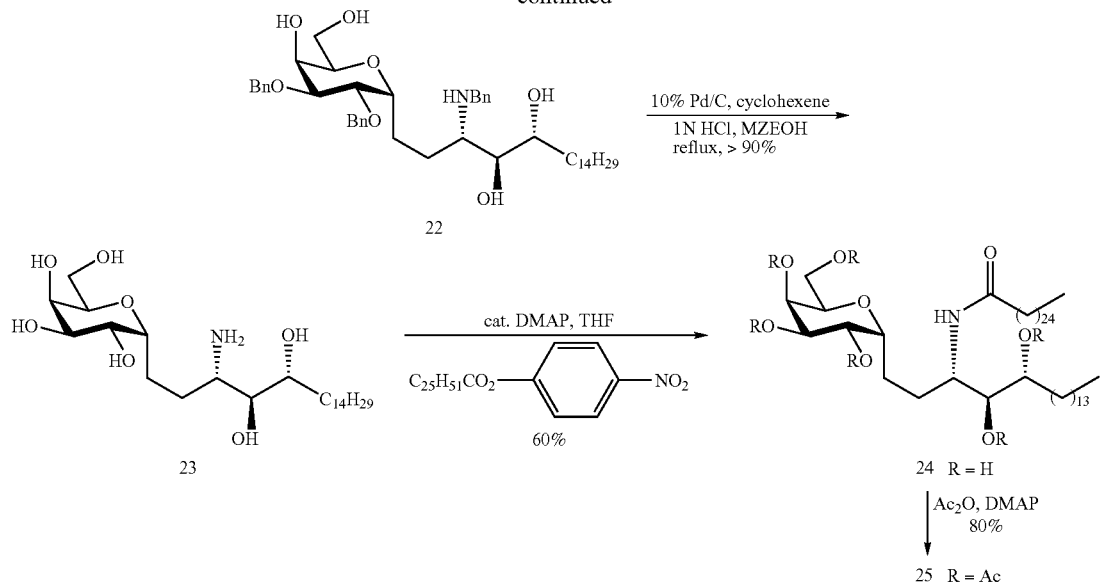

amide chain was then introduced using p-nitrophenyl hexadeconate as the acylating agent to afford the target 24 (Morita, M. et al., *J. Med. Chem.* 1995, 38, 2176-2187). Final purification was done by flash chromatography on silica gel eluting with CHCl$_3$: MeOH (4:1). The $^1$H and $^{13}$C NMR and optical rotation {[α]$^{25}_D$+40.8° (c=1.3, pyridine)}, mp 175-178° C., high resolution FABMS m/z 856.7601 (C$_{51}$H$_{101}$O$_8$N+H$^+$ requires 856.7605) obtained for a sample of 24. The mass spectrum and $^1$H NMR of fully acylated compound 25 further confirmed that 24 was the right compound, namely, CRONY-101.

Compounds from Synthesis of CRONY-101

L-2-[(benzyloxycarbonyl)amino]-4-hydroxybutyric Acid (1)

To a solution of L-homoserine 1 (4.0 g, 33.6 mmol) in 160 ml of 1N NaHCO$_3$ was added 6.0 ml (37 mmol) of benzyl chloroformate. The reaction mixture was stirred at 23° C. for 24 h and then extracted with ether (2×200 ml). The aqueous phase was ice cooled, carefully acidified to pH 2-3 with 3N HCl, and extracted with ethyl acetate (4×100 ml). The extract was dried over Na$_2$SO$_4$, filtered, and evaporated to afford 6.52 g (77%) product as a white solid. $^1$H NMR (Me$_2$CO-d$_6$, 300 MHz) δ 7.39-7.31 (m, 1H, C$_6$H$_5$), 6.63 (d, J=7.7 Hz, 1H, NH), 5.08 (s, 2H, CH$_2$Ph), 4.42 (m, 1H, CH), 3.70 (m, 2H, CH$_2$O), 2.05 (m, 1H), 1.91 (m, 1H).

Methyl-L-2-[(benzyloxycarbonyl)amino]-4-hydroxybutyrate (2)

To a solution of above compound (5.7 g, 22.5 mmol) in 50 ml MeOH was added dropwise 2M trimethylsilyldiazomethane in hexanes (22.5 ml, 25 mmol) at 0° C. The reaction mixture was stirred at room temperature (rt) overnight. Basic dowex resin was added, filtered and rinsed by methanol. After evaporation of the methanol in room temperature, the residue was purified by flash chromatography on florisil eluting with 50% PE/EtOAc to afford 4.6 g (77%) 2 as a colorless oil. $^1$H NMR (CDCl$_3$, 300 MHz): δ 7.35 (s, 5H, C$_6$H$_5$), 5.69 (d, J=6.6 Hz, 1H, NH), 5.12 (s, 2H, CH$_2$Ph), 4.55 (m, 1H), 3.76 (s, 3H, OMe), 3.70 (m, 2H), 2.81 (br, 1H, OH), 2.15 (m, 1H), 1.71 (m, 1H). $^{13}$C NMR(CDCl$_3$, 75 MHz): δ 174.09, 153.72, 136.21, 128.21, 128.61, 128.18, 67.42, 58.60, 52.77, 51.69, 35.33.

Methyl-L-2-[(benzyloxycarbonyl)amino]-4-O-(tert-butyldimethylsilyl)-butyrate

To a solution of 2 (4.19 g, 15.66 mmol) in 20 ml CH$_2$Cl$_2$ was added TBDMSCl (2.83 g, 18.8 mmol) followed by imidazole (2.55 g, 37.6 mmol). This reaction mixture was stirred at room temperature for 2 h. The mixture was filtered, rinsed by CH$_2$Cl$_2$ and washed with water. The solution was concentrated and purified by column chromatography on silica gel eluting with EtOAc-PE (30%) to afford 5.429 g (90%) product as a colorless oil. $^1$H NMR (CDCl$_3$, 300 MHz): δ 7.34 (s, 5H, C$_6$H$_5$), 5.93 (d, J=7.7 Hz, 1H, NH), 5.10 (m, 2H, CH$_2$Ph), 4.45 (m, 1H), 3.73 (s, 3H, OMe), 3.68 (m, 2H), 2.00 (m, 2H), 0.87 (s, 9H), 0.04 (s, 6H). $^{13}$C NMR(CDCl$_3$, 75 MHz): δ 172.72, 156.06, 136.35, 128.56, 128.12, 128.02, 66.99, 60.16, 52.88, 52.47, 34.13, 26.12, 18.46, −5.26.

L-2-[(benzyloxycarbonyl)amino]-4-O-(tert-butyldimethylsilyl)-butylaldehyde (3)

To a solution of above compound (5.42 g, 15.66 mmol) in 20 ml THF at −78° C. was added 1M DIBAL in heptane (43 ml, 42 mmol). The reaction mixture was stirred at −78° C. for 3 h. The resulting emulsion was slowly poured into 100 ml of ice-cold 1N HCl with stirring over 10 min, and the aqueous mixture was extracted with EtOAc (3×100 ml), dried over Na$_2$SO$_4$, filtered and concentrated in vacuo. The residue was purified by column chromatography on silica gel eluting with EtOAc-PE (20%) to afford 4.03 g (85%) 3 as a colorless oil. $^1$H NMR (CDCl$_3$, 300 MHz): δ 9.59 (s, 1H, CHO), 7.35 (m, 5H, C$_6$H$_5$), 5.86 (br, 1H, NH), 5.12 (s, 2H, CH$_2$Ph), 4.30 (m, 1H), 3.69 (t, 2H), 2.14 (m, 2H), 0.86 (s, 9H), 0.03 (s, 3H), 0.02

(s, 3H). $^{13}$C NMR (CDCl$_3$, 75 MHz), δ 199.01, 156.18, 136.41, 128.65, 128.29, 128.16, 67.20, 59.21, 59.13, 32.16, 26.09, 18.42, −5.21, −5.30.

Preparation of Z-Olefin (4)

To a suspension of pentadecylphosphonium bromide (5.52 g, 9.8 mmol; prepared from 1-bromopentadecane and triphenylphosphine, refluxed in toluene for 5 days, 98%) in THF (20 ml) was added dropwise NaHMDS (0.6M in toluene, 15 ml, 9.2 mmol) at −75° C. under nitrogen atmosphere. The solution was gradually warmed to 0° C. and stirred for 1 h. To this solution, which was cooled down to −75° C. again, aldehyde 3 (2.472 g, 7 mmol) in 8 ml THF was added dropwise over 30 min. After the reaction mixture was stirred at rt for 2 h, the reaction was quenched by addition of saturated NH$_4$Cl (100 ml) and extracted with ether. The organic extract was washed with brine, dried over Na$_2$SO$_4$, filtered and concentrated in vacuo. The residue was purified by column chromatography on silica gel eluting with EtOAc-PE (10%) to afford 3.44 g (85%) Z-olefin 4 as a colorless oil. $^1$H NMR (CDCl$_3$, 500 MHz): δ 7.34-7.31 (m, 5H, C$_6$H$_5$), 5.47 (after decoupling, d, J=10 Hz, 1H, vinyl H next to CH$_2$), 5.42 (m, 1H, NH), 5.27 (t, J=9.8 Hz, 1H, vinyl H next to CH), 5.09 (m, 2H, CH$_2$Ph), 4.58 (m, 1H), 3.67 (m, 2H), 2.1 (m, 2H), 1.73 (m, 2H), 1.25 (s, 22H), 0.89 (s, 12H), 0.05 (s, 3H), 0.04 (s, 3H). $^{13}$C NMR(CDCl$_3$, 75 MHz): δ 155.71, 136.96, 132.39, 129.96, 128.52, 128.16, 128.02, 66.59, 60.34, 60.31, 47.24, 38.06, 32.21, 29.99, 29.85, 29.69, 29.65, 29.55, 29.50, 27.96, 26.17, 22.99, 18.43, 14.42, −5.15.

Dihydroxylation of olefin (Z)-4 using AD-mix-β

To a solution of AD-mix-β (6.294 g) and methanesulfonamide (0.427 g, 4.50 mmol) in t-BuOH/H$_2$O (1:1, 10 ml) was added Z-4 (2.45 g, 4.49 mmol) at 0° C. under nitrogen atmosphere. The mixture was stirred at rt for 48 h, quenched with Na$_2$S$_2$O$_3$(6.7 g) and extracted with EtOAc. The organic extract was washed with 1N KOH, H$_2$O, brine and dried over Na$_2$SO$_4$. After evaporation of the solvent under the reduced pressure, the diols were purified by column chromatography (EtOAc/PE=30%) to give 6 (3,4 syn form, 0.5 g, 19% yield) and 5 (3,4-anti form, 1.7 g, 65% yield) as a white solid.

(3S,4R,5S)-1-O-(tert-butyldimethylsilyl)-3-[(benzyloxycarbonyl)amino-4,5-nonadecanediol (6)

mp 39-40° C. [α]$^{25}$ 3.0° (c 9, CHCl$_3$). $^1$H NMR (CDCl$_3$, 300 MHz): δ 6.36 (s, 5H, C$_6$H$_5$), 5.29 (d, J=8.8 Hz, 1H, NH), 5.01 (s, 2H, CH$_2$Ph), 4.16 (m, 1H), 3.73 (t, J=5.6 Hz, 2H), 3.59 (br, 1H), 3.34 (m, 2H), 3.04 (d, J=4.0 Hz, 1H), 1.86 (m, 2H), 1.73 (m, 1H), 1.55 (m, 1H), 1.26 (s, 24H), 0.89 (s, 12H), 0.06 (s, 6H). $^{13}$C NMR(CDCl$_3$, 75 MHz): δ 157.64, 136.38, 128.68, 128.35, 128.22, 76.43, 71.53, 67.38, 60.08, 50.22, 49.86, 35.46, 33.52, 32.23, 30.10, 30.00, 29.96, 29.66, 26.11, 23.00, 18.43, 14.43, −5.20, −5.23.

(3S,4S,5R)-1-O-(tert-butyldimethylsilyl)-3-[(benzyloxycarbonyl)amino-4,5-nonadecanediol (5)

mp 40-43° C. [α]$^{25}$ 16.3° (c 9, CHCl$_3$). $^1$H NMR (CDCl$_3$, 300 MHz): δ 7.38 (s, 5H, C$_6$H$_5$), 5.61 (d, J=8.0 Hz, 1H, NH), 5.08 (s, 2H, CH$_2$Ph), 4.09 (m, 1H), 3.73 (m, 3H), 3.57 (m. 1H), 3.49 (m, 1H), 2.11 (br, 1H), 1.95-1.76 (m, 12H), 1.26 (s, 26H), 0.89 (s, 12H), 0.07 (s, 6H). $^{13}$C NMR(CDCl$_3$, 75 MHz): δ 156.41, 136.57, 128.58, 128.17, 128.12, 76.26, 73.22, 66.95, 59.98, 51.36, 33.77, 32.19, 32.05, 29.63, 26.12, 26.04, 22.96, 18.44, −5.20, −5.27.

(3S,4S,5R)-1-O-(tert-butyldimethylsilyl)-3-[(benzyloxycarbonyl)amino-4,5-O-isopropylidene-nonadecane (7)

To a solution of diol 5 (2.23 g, 3.85 mmol) in 30 ml CH$_2$Cl$_2$ was added 2,2-dimethoxy propane (2.37 ml, 19.3 mmol) followed by PPTs (97 mg, 0.38 mmol). After the reaction mixture was stirred at rt for 1.5 h, 50 ml saturated NaHCO$_3$ was added and extracted with CH$_2$Cl$_2$(30 ml×2). The organic phase was dried over Na$_2$SO$_4$. After evaporation of the solvent under the reduced pressure, the residue was purified by column chromatography (EtOAc/PE=10%) to give product 7 (2.287 g, 96% yield) as an oil. $^1$H NMR (CDCl$_3$, 300 MHz): δ 7.34 (s, 5H, C$_6$H$_5$), 5.17 (d, J=8.8 Hz, 1H, NH), 5.07 (s, 2H, CH$_2$Ph), 4.13 (m, 2H), 3.90 (m, 1H), 3.78-3.70 (m, 2H), 1.89 (m, 2H), 1.56 (m, 2H), 1.43 (s, 3H), 1.33 (s, 3H), 1.25 (s, 24H), 0.88 (s, 12H), 0.04 (s, 3H), 0.03 (s, 3H). $^{13}$C NMR (CDCl$_3$, 75 MHz): δ 155.86, 136.77, 128.47, 128.02, 107.78, 79.39, 77.96, 66.68, 60.25, 49.19, 34.40, 32.16, 29.92, 29.59, 29.12, 27.44, 27.01, 26.13, 25.61, 22.92, 18.39, 14.35, −5.25, −5.28.

(3S,4S,5R)-3-[(benzyloxycarbonyl)amino-4,5-O-isopropylidene-nonadecanol (8)

To a solution of above compound (3.31 g, 5.33 mmol) in 25 ml THF was added 1M Bu$_4$NF in THF (12 ml) followed by 0.5 ml acetic acid. After the reaction mixture was stirred at rt overnight, 20 ml saturated NaHCO$_3$ was added and extracted with CH$_2$Cl$_2$(50 ml×2). The organic phase was dried over Na$_2$SO$_4$. After evaporation of the solvent under the reduced pressure, the residue was purified by column chromatography (EtOAc/PE=50%) to give 8 (2.56 g, 90% yield) as a white solid. Mp 58-60° C. [a]$^{25}$ 3.67° (c 3, CHCl$_3$). $^1$H NMR (CDCl$_3$, 300 MHz): δ 7.36 (s, 5H, C$_6$H$_5$), 5.11 (s, 2H, CH$_2$Ph), 4.86 (br, 1H, NH), 4.12 (m, 1H), 4.03-3.92 (m, 2H), 3.72 (m, 2H), 2.82 (br, 1H, OH), 2.02 (m, 2H), 1.52 (m, 24H), 1.44 (s, 3H), 1.33 (s, 3H), 0.88 (t, J=6.6 Hz, 3H). $^{13}$C NMR (CDCl$_3$, 75 MHz): δ 156.91, 136.38, 128.72, 128.41, 128.22, 108.28, 79.78, 78.03, 77.44, 77.39, 77.02, 67.38, 59.06, 48.70, 35.36, 32.21, 30.16, 29.99, 29.90, 29.85, 29.65, 29.25, 27.04, 25.74, 22.98, 14.42.

(3S,4S,5R)-1-iodo-3-[(benzyloxycarbonyl)amino-4, 5-O-isopropylidene-nonadecane (9)

A mixture of 8 (2.5 g, 4.95 mmol), PPh$_3$(1.63 g, 6.1 mmol), imidazole (0.87 g, 11.8 mmol) and iodine (2.03 g, 7.4 mmol) in THF (50 ml) was stirred under reflux for 2.5 h. After evaporation of the solvent, the crude product was dissolved in CH$_2$Cl$_2$(100 ml) and solids were removed by filtration. An equal volume of saturated aqueous NaHCO$_3$ was added and the mixture was stirred for 10 min. Iodine was added in portions and when the organic phase remained iodine-colored, the mixture was stirred for an additional 10 min. Excess iodine was destroyed by the addition of saturated aqueous Na$_2$S$_2$O$_3$ solution. The organic layer was diluted with CH$_2$Cl$_2$ (50 ml), separated, washed with water (50 ml), dried over Na$_2$SO$_4$. After evaporation of the solvent under the reduced pressure, the residue was purified by column chromatography (EtOAc/PE=20%) to give 9 (2.57 g, 87% yield) as a white solid. Mp 79-81° C.

$^1$H NMR (CDCl$_3$, 300 MHz): δ 7.33 (s, 5H, C$_6$H$_5$), 5.07 (m, 34.05 (m, 3H), 3.78 (m, 1H), 3.23 (m, 2H), 2.26 (m, 2H), 1.89 (m, 2H), 1.42 (s, 3H), 1.30 (s, 3H), 1.55-1.26 (m, 24H), 0.88 (t, J=6.6 Hz, 3H). $^{13}$C NMR (CDCl$_3$, 75 MHz): δ 155.88, 136.35, 128.59, 128.26, 128.21, 108.11, 79.57, 77.75, 67.11, 52.56, 36.72, 32.14, 30.35, 30.26, 29.91, 29.81, 29.76, 29.58, 29.15, 27.36, 26.99, 25.51, 22.91, 14.37.

(3'S,4'S,5'R) 3'-[(benzyloxycarbonyl)amino-4',5'-O-isopropylidene-nonadecanylthio] 2,3,4,6-tetra-O-acetyl-β-D-galactopyranose (11)

To a degassed solution of 2.02 g (4.98 mmol) β-2,3,4,6-tetra-O-acetyl-galactosyl thioacetate 10 in 15 ml DMF, NH$_2$NH$_2$.HOAc (0.47 g, 5.96 mmol) was added. This solution was degassed at room temperature for 1 h. Iodide 9 (2.55 g, 4.14 mmol) was added, followed by triethyl amine (0.64 ml, 6.58 mmol). After 2 h, 100 ml ethyl acetate and 50 ml water were added. The organic layer was washed with water and brine, and dried over anhydrous sodium sulfate. After evaporation of the organic solvent, the residue was purified by chromatography on silica gel eluting with 50% EtOAc/PE to afford 3.2 g β-thiogalactoside 11 (90% yield) as a sticky oil.

$^1$H NMR (300 MHz, CDCl$_3$): δ 7.32 (s, 5H), 5.42 (d, J=3.0 Hz, 1H, H-4), 5.24 (t, J=9.9 Hz, 1H, H-2), 5.10 (m, 2H), 5.03 (dd, J=3.3, 9.9 Hz, 1H, H-3), 4.83 (d, J=9.5 Hz, 1H, NH), 4.46 (d, J=9.9 Hz, 1H, H-1), 4.13 (m, 3H), 4.04 (t, J=5.8 Hz, 1H, H-5), 3.94 (t, 1H), 3.79 (m, 1H), 2.85-2.72 (m, 2H, H—SCH$_2$), 2.12 (s, 3H, H-OAc), 2.05 (s, 3H, H-OAc), 2.04 (s, 3H, H-OAc), 1.98 (s, 3H, H-OAc), 1.76 (m, 1H), 1.54 (m, 1H), 1.43 (s, 3H), 1.32 (s, 3H), 1.26 (s, 24H), 0.88 (t, J=6.6 Hz, 3H). $^{13}$C NMR (75 MHz, CDCl$_3$): δ 170.27, 170.21, 170.04 169.56, 155.77, 136.49, 128.60, 128.24, 128.12, 108.09, 84.30, 77.77, 77.45, 77.05, 76.96, 74.62, 72.05, 67.38, 67.32, 66.99, 61.43, 50.97, 32.44, 32.14, 30.26, 30.18, 29.92, 29.82, 29.28, 27.55, 26.95, 26.78, 26.75, 25.64, 22.91, 21.02, 20.87, 20.84, 14.35.

(3'S,4'S,5'R) 3'-[(benzyloxycarbonyl)amino-4',5'-O-isopropylidene-nonadecanylthio]4,6-O-benzylidene-β-D-galactopyranose (12)

Into the solution of 2.31 g (2.71 mmol) of 2,3,4,6-tetra-O-acetyl-β-thio-galacoside 11 and 50 ml Methanol was added NaOMe (70 mg, 1.3 mmol). The mixture was stirred at rt. until a white precipitate was formed. The precipitate was dissolved in EtOAc, then acidic resin was added until the pH of the solution is neutral. The resin was filtered off and rinsed by EtOAc. The solution was concentrated until completely dry to afford 1.76 g of a white solid. To a mixture of above solid (1.75 g, 2.57 mmol), p-methoxybenzaldehyde dimethyl acetal (1.1 ml, 6.42 mmol), and 50 ml dry CH$_2$Cl$_2$ and 3 ml DMF was added p-toluene sulfonic acid monohydrate (29 mg) at room temperature. After 2 h, the mixture was neutralized with triethyl amine (1 ml) and concentrated. The residue was chromatographed (SiO$_2$, EtOAc/MeOH, 100% to 95%) to give 12 (1.72 g, 86% overall yield) as a white solid. $^1$H NMR (300 MHz, CDCl$_3$): δ 7.48 (d, J=8.8 Hz, 2H), 7.29 (m, 5H), 6.82 (d, J=8.8 Hz, 2H), 5.43 (s, 1H), 5.06 (m, 3H), 4.17 (d, 2H), 4.16 (s, 1H), 4.05 (m, 3H), 3.90 (m, 3H), 3.75 (s, 3H), 3.61 (m, 2H), 3.39 (s, 1H), 2.89 (m, 1H), 2.68 (m, 1H), 2.05 (m, 2H), 1.80 (m, 2H), 1.60-1.20 (m, 30H), 0.88 (t, 3H). $^{13}$C NMR (75 MHz, CDCl$_3$): δ 160.14, 156.19, 136.45, 130.37, 128.56, 128.16, 128.08, 127.75, 113.61, 108.03, 101.17, 85.69, 79.64, 77.76, 75.74, 73.88, 70.19, 69.33, 68.98, 67.00, 55.38, 50.59, 32.62, 32.09, 29.88, 29.79, 29.73, 29.53, 29.11, 27.50, 26.95, 25.63, 25.33, 22.87, 14.33.

(3'S,4'S,5'R) 3'-[(benzyloxycarbonyl)benzylamino-4', 5'-O-isopropylidene-nonadecanylthio]4,6-O-benzylidene-2,3-di-O-benzyl-β-D-galactopyranose β-S-galactoside 12 (1.49 g, 1.86 mmol) was dissolved in 20 ml THF and 5 ml DMF, NaH (0.6 g, 60% in mineral oil) was added, the mixture was stirred at rt. for ½ h, then 0.068 g (0.186 mmol) tetra-butylammonium iodide was added followed by 0.89 ml benzyl bromide (7.44 mmol). After the mixture was stirred at room temperature overnight, the reaction was quenched with 10 ml of MeOH. The resulting solution was added to 50 ml H$_2$O and extracted by EtOAc (100 ml×3). The organic phase was washed by brine, and dried over Na$_2$SO$_4$ and concentrated. The residue was chromatographed on a column of silica gel (eluted with 30% EtOAc-petroleum ether) to afford 1.62 g product (83%) as a colorless oil. MS: m/z 1094(M$^+$+Na$^+$), (calcd. C$_{65}$H$_{85}$O$_{10}$SN, 1071). $^1$H NMR (300 MHz, CDCl$_3$): δ 7.48 (d, J=8.8 Hz, 2H), 7.43-7.22 (m, 20H), 6.88 (d, J=8.8 Hz, 2H), 5.46 (s, 1H), 5.17 (m, 2H), 4.78 (m, 6H), 4.34 (m, 4H), 4.16 (d, J=3.3 Hz, 1H), 4.14 (m, 1H), 3.95 (m, 1H), 3.79 (s, 3H), 3.59 (dd, J=3.3, 9.1 Hz, 1H), 3.50 (m, 1H), 3.29 (m, 1H), 2.70 (m, 2H), 2.06 (m, 2H), 1.47-1.13 (m, 32H), 0.92 (t, 3H). $^{13}$C NMR (75 MHz, CDCl$_3$): δ 160.06, 158.66, 139.19, 138.55, 138.41, 136.43, 130.64, 128.41, 128.33, 128.09, 127.84, 127.78, 127.67, 127.50, 127.34, 127.31, 127.21, 127.08, 113.57, 107.69, 101.33, 81.23, 79.64, 79.59, 79.42, 77.88, 75.79, 73.99, 71.77, 69.99, 69.40, 55.41, 32.14, 30.99, 30.08, 29.92, 29.85, 29.63, 29.57, 27.74, 25.54, 22.91, 14.35.

(3'S,4'S,5'R) 3'-[(benzyloxycarbonyl)benzylamino-4', 5'-O-isopropylidene-nonadecanylsulfonyl] 4,6-O-benzylidene-2,3-di-O-benzyl-β-D-galactopyranose (13)

A solution of MMPA (2.1 g, 4.26 mmol) in H$_2$O (10 ml) was added to a solution of thio-galactoside (1.52 g, 1.42 mmol) in EtOH (10 ml) and THF (10 ml), the mixture was kept at 60° C. for 3 h. The mixture was concentrated in vacuo to dryness. The residue was treated with 50 ml saturated NaHCO$_3$ solution, and extracted with EtOAc (50 ml×3), dried over Na$_2$SO$_4$ and evaporated to dryness. The residue was purified by chromatography on silica gel eluting with 40% EtOAc/PE to afford pure sulfone 13 (1.45 g, 93%) as a white solid. mp. 40-43° C. MS: m/z 1121(M$^+$+NH$_4^+$), (calcd. C$_{65}$H$_{85}$O$_{12}$SN, 1103). $^1$H NMR (CDCl$_3$, 400 MHz heated at 55° C.): δ 7.46-7.18 (m, 22H), 6.88 (d, J=8.8 Hz, 2H), 5.39 (s, 1H), 5.13 (s, 2H), 4.95 (d, 1H), 4.84 (d, 1H), 4.73 (s, 2H), 4.65 (m, 1H), 4.42 (t, J=9.6 Hz, 1H), 4.30 (m, 2H), 4.24 (s, 1H), 4.22 (d, 2H), 4.11 (d, 1H), 4.07 (m, 1H), 3.91 (dd, 1H), 3.79 (s, 3H), 3.66 (dd, 1H), 3.55 (b, 1H), 3.32 (s, 1H), 3.28 (b, 1H), 3.00 (b, 1H), 2.35 (m, 1H), 2.20 (b, 1H), 1.34 (s, 3H), 1.25 (s, 28H), 1.17 (s, 3H), 0.89 (t, 3H). $^{13}$C NMR (75 MHz, CDCl$_3$): δ 160.39, 156.97, 138.64, 138.07, 136.21, 130.39, 128.81, 128.68, 128.60, 128.43, 128.06, 127.90, 127.72, 127.59, 113.86, 107.98, 101.59, 80.80, 78.93, 77.93, 77.42, 76.58, 75.78, 73.27, 73.11, 72.10, 70.71, 68.92, 55.56, 32.21, 30.00, 29.96, 29.92, 29.65, 28.03, 26.36, 25.67, 22.98, 14.41.

(3'S,4'S,5'R) 3'-[(benzyloxycarbonyl)benzylamino-4', 5'-O-isopropylidene] 4,6-O-benzylidene-2,3-di-O-benzyl-β-D-galactopyranosylidene nonadecane (14)

To a solution of 1.45 g 13 (1.32 mmol) in 10 ml t-BuOH and 10 ml CF$_2$BrCF$_2$Br, 4 g 25% (by weight) KOH/Al$_2$O$_3$ (prepared one day earlier) was added. This mixture was refluxed at 47° C. for 10 h. The solution was filtered through a pad of celite which was washed by CH₂Cl₂. The residue was purified by column chromatography on silica gel eluting with 25% EtOAc-PE to afford 0.6 g 14 (60% based on recovered starting material) as a colorless oil. MS: m/z 1060(M⁺+Na⁺), (calcd. C₆₅H₈₃O₁₀N, 1037). ¹H NMR (300 MHz, CDCl₃), δ 7.46 (d, J=8.8 Hz, 2H), 7.39-7.10 (m, 20H), 6.87 (d, J=8.8 Hz, 2H), 5.50 (s, 1H), 5.40 (t, 1H), 5.13 (m, 2H), 4.97 (d, 1H), 4.82-4.66 (m, 5H), 4.52 (m, 1H), 4.40-4.24 (m, 3H), 4.09-3.99 (m, 2H), 3.79 (s, 3H), 3.72 (m, 1H), 3.58 (m, 1H), 3.48 (m, 1H), 2.54 (t, 2H), 1.41-1.12 (m, 32H), 0.89 (t, 3H).

Benzoate (15)

To a solution of 0.6 g 14 (Z+E, 0.578 mmol) in 10 ml MeOH, TMSCI (73 µl) was added at 0° C. After the mixture was stirred at 0° C. for 30 min, 20 ml saturated NaHCO₃ was added. The mixture was extracted with CH₂Cl₂ (2×40 ml). The organic phase was dried over Na₂SO₄, concentrated, the residue was purified by column chromatography on silica gel eluting with 35% EtOAc-PE to afford 0.36 g product (66%). ¹H NMR (300 MHz, CDCl₃): δ 7.28 (m, 20H), 5.08 (m, 2H), 4.90 (d, 1H), 4.68 (s, 2H), 4.61 (d, 1H), 4.56 (d, 1H), 4.51 (d, 1H), 4.35 (d, 1H), 4.02-3.95 (m, 4H), 3.84-3.81 (m, 3H), 3.65 (m, 1H), 3.58 (m, 1H), 3.00 (s, 3H), 2.59 (br, 1H), 2.23 (br, 1H), 1.51 (m, 4H), 1.39 (s, 3H), 1.33 (s, 26H), 1.20 (s, 3H), 0.89 (t, 3H).

To a solution of above compound 0.36 g (0.378 mmol) in 10 ml CH₂Cl₂, BzCl (66 µl, 0.56 mmol) was added at 0° C., followed by Et₃N (0.3 ml, 2.3 mmol). After the mixture was stirred at 0° C. for 2 h, 20 ml 10% ammonia solution was added. The mixture was extracted with CH₂Cl₂ (2×40 ml). The organic phase was dried over Na₂SO₄, concentrated, the residue was purified by column chromatography on silica gel eluting with 25% EtOAc-PE to afford 0.365 g product 15 (92%).

To a solution of 0.365 g 15 (0.347 mmol) in 10 ml MeOH, 1N HCl/Et₂O (1 ml) was added at 0° C. After the mixture was stirred at 0° C. for 2 h, 20 ml saturated NaHCO₃ was added. The mixture was extracted with CH₂Cl₂ (2×40 ml). The organic phase was dried over Na₂SO₄, and concentrated, the residue was purified by column chromatography on silica gel eluting with 30% EtOAc-PE to afford 0.275 g product 16 (80%). ¹H NMR (300 MHz, CDCl₃): δ 7.92 (d, J=7.3 Hz, 2H), 7.53 (t, 1H), 7.39-7.20 (22H), 5.15 (d, 1H), 4.94 (m, 2H), 4.74-4.69 (m, 3H), 4.63 (br, 1H), 4.55 (m, 2H), 4.43 (br, 1H), 4.08-3.93 (m 5H), 3.55 (d, 1H), 3.42 (m, 1H), 3.11 (s, 3H), 2.17 (br, 1H), 1.76 (m, 2H), 1.47 (m, 2H), 1.25 (s, 26H), 0.89 (t, 3H). ¹³C NMR (75 MHz, CDCl₃): δ 166.35, 157.80, 138.54, 136.34, 133.09, 130.21, 129.82, 129.71, 128.66, 128.60, 128.48, 128.43, 128.22, 128.04, 127.96, 127.79, 127.60, 103.18, 79.89, 79.05, 75.91, 75.58, 73.17, 72.60, 69.34, 68.17, 67.83, 64.57, 47.81, 33.80, 33.78, 32.18, 29.96, 29.60, 27.81, 25.89, 22.93, 14.30.

Cyclic Carbonate

To a solution of 0.27 g 16 (0.266 mmol) in 4 ml CH₂Cl₂ and pyridine 0.13 ml, 40 mg (0.133 mmol) triphosgene in 1 ml CH₂Cl₂ was dropwide added at −70° C. After the addition was finished, the reaction mixture was warmed up to room temperature. After 1.5 h, the mixture was diluted with CH₂Cl₂ (30 ml), quenched with 20 ml saturated NH₄Cl, then extracted with CH₂Cl₂ (20 ml×30). The organic phase was washed with 1N HCl, saturated NaHCO₃, and brine. The organic layer was dried over Na₂SO₄, concentrated, the residue was purified by column chromatography on silica gel eluting with 20% EtOAc-PE to afford 0.265 g product (90%). ¹H NMR (300 MHz, CDCl₃): δ 8.06 (d, J=7.3 Hz, 2H), 7.58 (t, 1H), 7.46 (t, 2H), 7.36-7.24 (m, 19H), 7.05 (m, 1H), 5.16 (m, 2H), 4.99 (d, 1H), 4.71-4.49 (m, 8H), 4.32 (m, 1H), 4.09 (m, 1H), 4.03 (dd, 1H), 3.90 (m, 1H), 3.82 (m, 2H), 3.14-3.05 (two singlets, 3H), 2.48 (s, 1H), 1.85 (m, 1H), 1.66 (m, 3H), 1.46 (m, 2H), 1.27 (s, 24H), 0.89 (t, 3H). ¹³C NMR (75 MHz, CDCl₃): δ 166.41, 156.85, 153.62, 138.54, 138.47, 138.34, 138.32, 138.04, 136.19, 133.13, 129.82, 128.87, 128.72, 128.56, 128.35, 128.25, 128.13, 128.08, 127.97, 127.84, 127.75, 127.61, 127.57, 127.52, 101.95, 80.64, 79.96, 79.85, 77.48, 77.42, 77.11, 77.02, 76.90, 75.41, 72.53, 69.30, 68.24, 67.69, 64.35, 55.47, 48.21, 32.28, 32.20, 29.97, 29.79, 29.73, 29.61, 29.19, 28.92, 28.47, 25.66, 22.93, 14.30.

Silyl Ether (17)

To a solution of 260 mg above material (0.249 mmol) in 5 ml DMF, i-Pr₂SiHCl 0.13 ml (0.75 mmol) and 101 mg imidazole were added. After the mixture was stirred at rt for 2 h, the solution was concentrated and purified by column chromatography on silica gel eluting with 30% EtOAc-PE to afford 0.228 g 17 (87%) as a colorless oil. MS: m/z 1173(M⁺+NH₄+), (calcd. C₆₉H₉₃O₁₂SiN, 1155). ¹H NMR (300 MHz, CDCl₃), δ 8.06 (d, 7.3 Hz, 2H), 7.59 (t, 1H), 7.47 (t, 2H), 7.40-7.29 (m, 19H), 7.04 (m, 1H), 5.15 (m, 2H), 5.01 (d, 1H), 4.80 (d, 1H), 4.65 (m, 2H), 4.54-4.32 (m, 7H), 3.99 (m, 2H), 3.89 (m, 1H), 3.80 (m, 2H), 3.16-3.06 (two singlets, 3H), 1.92 (m, 1H), 1.69 (m, 1H), 1.47 (m, 2H), 1.27 (s, 26H), 1.07 (m, 14H), 0.89 (t, 3H). ¹³C NMR (75 MHz, CDCl₃): δ 166.35, 156.88, 153.54, 138.68, 138.32, 133.15, 132.36, 130.36, 129.79, 128.91, 128.57, 127.47, 128.39, 128.22, 128.08, 127.90, 127.77, 127.70, 127.57, 127.51, 127.44, 127.40, 127.35, 101.95, 80.71, 80.29, 79.68, 77.43, 77.38, 77.11, 77.02, 76.98, 75.56, 73.16, 71.56, 70.55, 68.28, 64.55, 48.13, 32.21, 29.97, 29.93, 29.79, 29.71, 29.62, 29.26, 28.97, 25.57, 22.94, 17.95, 17.91, 17.84, 17.77, 14.31, 13.22, 13.16.

α-C-glycoside (20)

Syringe pump addition of a solution (92 mg, 0.079 mmol 17 in 6 ml CH₂Cl₂) to a solution of BF₃.Et₂O (50 µl, 0.4 mmol) in 6 ml CH₂Cl₂ was carried out over a 5 h reaction time. The mixture was then treated with 20 ml sat. NaHCO₃, and extracted with CH₂Cl₂ (20 ml×3). The organic solvent was concentrated to afford a mixture of 18 and 19.

To the above crude products in 5 ml THF and 30 µl acetic acid, 0.4 ml 1N Bu₄NF was added. The reaction was stirred at rt for 1 h, the mixture was diluted with CH₂Cl₂, washed with water. The organic was dried over Na₂SO₄, concentrated, the residue was purified by column chromatography on silica gel eluting with 20% EtOAc-PE to afford 61 mg product 20 (76%) and 18 mg side product 19 (20%). MS: m/z 1029(M⁺+NH₄+), (calcd. C₆₆H₇₇O₁₁N, 1011). ¹³C NMR (75 MHz, CDCl₃): δ 166.54, 156.86, 153.59, 138.48, 138.30, 138.12, 136.17, 133.10, 130.36, 129.84, 128.89, 128.71, 128.61, 128.49, 128.41, 128.27, 128.23, 128.12, 127.95, 127.85, 127.68, 80.54, 79.76, 77.76, 77.50, 77.43, 76.22, 73.67, 73.03, 72.94, 70.30, 68.32, 67.53, 63.83, 55.20, 32.18, 29.96, 29.78, 29.66, 29.60, 29.23, 28.92, 25.52, 23.06, 22.93, 14.30.

Oxazolidinone (21)

Carbonate 20 (66 mg, 0.065 mmol) was dissolved in 5 ml dioxane:H₂O (1:1) and treated with NaOH 0.46 g and heated under reflux conditions at 90° C. overnight. The sample was concentrated in vacuo and redissolved in CHCl₃ and washed with saturated NH₄Cl solution. The aqueous layer was extracted with CHCl₃ (20 ml×3). The organic was dried over Na₂SO₄, concentrated, the residue was dried in vacuo to afford. 50 mg product 21 (96%). MS: m/z 774(M⁺+H⁺), (calcd. C₄₇H₆₇O₈N, 773). ¹H NMR (500 MHz, CDCl₃): δ 7.35-7.26 (m, 15H), 4.84 (d, J=15.0 Hz, 1H), 4.73 (m, 2H), 4.67 (d, J=10.0 Hz, 1H), 4.56 (d, J=11.5 Hz, 1H), 4.21 (t, J=8.5 Hz, 1H), 4.05 (d, J=15.0 Hz, 1H), 3.96-3.87 (m, 4H), 3.82 (t, J=7.5 Hz, 1H), 3.66 (d, J=10.0 Hz, 1H), 3.60 (m, 1H), 3.54 (dd, J=3.0, 8.5 Hz, 1H), 3.47 (m, 1H), 2.53 (br, 2H, OH), 2.36 (br, 1H, OH), 1.98 (m, 1H), 1.78 (m, 1H), 1.69 (m, 2H), 1.57 (m, 2H), 1.42 (m, 2H), 1.25 (m, 22H), 0.88 (t, J=6.5 Hz, 3H). $^{13}$C NMR (75 MHz, CDCl$_3$): δ 157.97, 138.50, 138.06, 128.92, 128.67, 128.58, 128.16, 127.96, 127.85, 79.49, 78.14, 76.23, 74.51, 73.81, 72.76, 71.08, 68.91, 68.41, 63.28, 57.34, 46.80, 34.99, 32.17, 29.94, 29.59, 24.94, 24.45, 22.92, 22.13, 14.30.

Benzylamine (22)

The crude compound 21 (50 mg, 0.063 mmol) was dissolved in 5 ml EtOH and 1 ml H$_2$O and treated with KOH (0.5 g) at reflux overnight. The cooled solution was diluted with saturated NH$_4$Cl solution and extracted with EtOAc (20 ml×3). The organic extracts were dried over Na$_2$SO$_4$, filtered, and concentrated, the residue was purified by column chromatography on silica gel eluting with CHCl$_3$:MeOH (4:1) to afford 39 mg product 22 (80%). MS: m/z 478(M$^+$+H$^+$), (calcd. C$_{46}$H$_{69}$O$_7$N, 477). $^1$H NMR (300 MHz, CDCl$_3$): δ 7.35-7.25 (m, 15H), 4.76-4.70 (m, 3H), 4.59 (d, J=11.7 Hz, 1H), 3.97-3.85 (m, 4H), 3.77 (s, 2H), 3.69 (dd, J=3.6, 12.1 Hz, 1H), 3.60 (m, 3H), 3.52 (m, 1H), 3.30 (t, J=6.6 Hz, 1H), 2.79 (br, 5H), 1.88 (m, 1H), 1.73 (m, 2H), 1.57 (m, 2H), 1.25 (s, 25H), 0.89 (t, J=6.9 Hz, 3H). $^{13}$C NMR (75 MHz, CDCl$_3$): δ 138.56, 138.19, 128.70, 128.58, 128.51, 128.17, 128.12, 127.95, 127.87, 127.43, 78.06, 76.48, 74.60, 74.42, 73.99, 73.84, 72.79, 71.34, 68.53, 68.50, 68.12, 67.70, 63.14, 60.97, 51.85, 34.66, 32.20, 30.18, 29.99, 29.63, 25.76, 25.69, 22.95, 21.91, 14.33.

3'S,4'S,5'R-3'-N-hexacosanoyl-4',5'-dihydroxynonadecyl-α-C-D-galactopyranoside (24)

A solution of benzylamine 22 (39 mg, 0.052 mmol) in 1 ml MeOH was treated with 10% Pd/C (40 mg), 1N HCl (52 μl, 0.052 mmol), and cylcohexene (0.2 ml).[12] The resulting slurry was heated at reflux for 4 h, then cooled to room temperature, filtered through a pad of celite and basic resin, and concentrated to give 23 mg of crude 23. A solution of this material in THF (1 ml) was treated with p-nitrophenyl hexacosanoate[13] (75 mg, 0.144 mmol) and a crystal of DMAP. The resulting solution was stirred at rt for 48 h and concentrated. The residue was purified by column chromatography on silica gel eluting with CHCl$_3$:MeOH (4:1) to afford 23 mg product 24 (60%) as a white solid. Mp: 175-178° C. [a]$^{25}$ 40.8° (c 1.3, pyridine). FABMS (high-res.): m/z (calcd. C$_{51}$H$_{101}$O$_8$N+H$^+$, 856.7605. found 856.7601). $^1$H NMR (500 MHz, C$_5$D$_5$N): δ 8.47 (d, J=8.8 Hz, 1H, NH), 6.78-6.00 (br, 6H, OH), 5.14 (m, 1H), 4.74 (dd, J=5.5, 8.8 Hz, 1H), 4.52 (m, 3H), 4.37 (dd, J=4.3, 11.0 Hz, 1H), 4.25 (m, 4H), 2.72 (m, 1H), 2.59 (m, 1H), 2.48 (m, 3H), 2.33 (m, 2H), 2.22 (m, 1H), 1.94 (m, 2H), 1.86 (m, 3H), 1.71 (m, 1H), 1.37 (s, 64H), 0.88 (t, J=6.4 Hz, 6H). $^{13}$C NMR (100 MHz, C$_5$D$_5$N): δ 173.36, 78.37, 76.90, 73.65, 72.53, 72.07, 70.46, 70.27, 62.61, 52.56, 36.86, 34.33, 32.00, 30.26, 30.07, 29.88, 29.70, 29.49, 26.42, 22.81, 14.15.

3S,4'S,5'R-3'-N-hexacosanoyl-4',5'-di-O-acetyinonadecacyl-2,3,4,6-tetra-O-acetyl-α-C-D-galactopyranoside (25)

To a solution of 24 (6 mg, 5.86 pmol) in 1 ml EtOAc, Ac$_2$O (15 μl, 0.158 mmol) and DMAP (1 mg, 8.191 mol) were added. The mixture was stirred at rt overnight. The residue was purified by column chromatography on silica gel eluting with EtOAc:PE (40%) to afford 5 mg product 25(80%). MS: m/z (M$^+$+H+), 1108, (M$^+$+Na$^+$), 1130, (calcd. C$_{63}$H$_{113}$O$_{14}$N, 1107). $^1$H NMR (500 MHz, C$_6$D$_6$): δ 5.56 (m, 2H), 5.42 (dd, J=3.0, 9.0 Hz, 1H), 5.27 (d, J=9.0 Hz, 2H), 5.16 (d, J=10.0 Hz, 1H), 4.46 (m, 2H), 4.33 (m, 1H), 4.10 (dd, J=5.0, 11.5 Hz, 1H), 3.74 (m, 1H), 2.01 (m, 3H), 1.83 (s, 3H), 1.81 (s, 3H), 1.78 (s, 3H), 1.73 (s, 3H), 1.70 (s, 3H), 1.62 (s, 3H), 1.45 (m, 1H), 1.35-1.31 (m, 74H), 0.90 (m, 6H).

The following Examples illustrate the invention without limiting its scope.

EXAMPLES

FIG. 1 depicts the adjuvant effects of the α-GalCer on DNA vaccination in mice. FIG. 1 demonstrates the enhancement of HIV specific CD4+/CD8+ T-cell responses.

Figure 2:
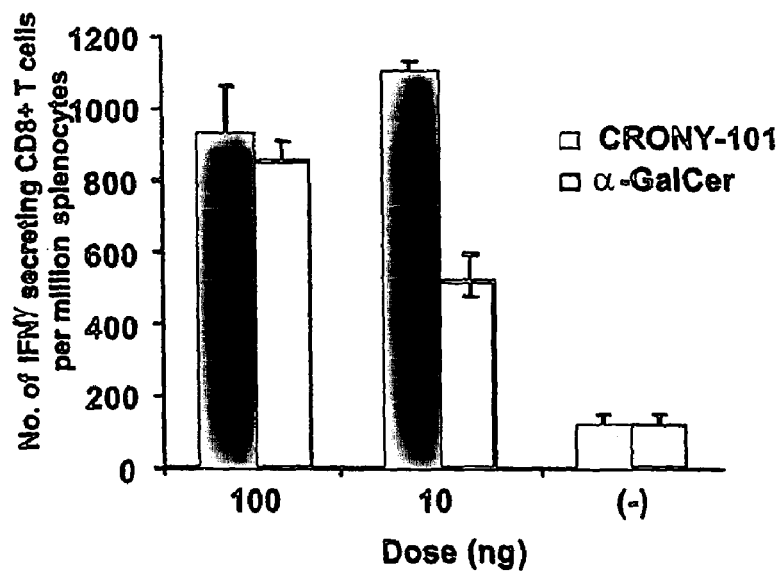

The inventors have now found that the α-C-GalCer compounds of formula I display utility as an adjuvant for modulating acquired immunity. FIG. 2 shows that the α-C-GalCer compound CRONY 101 exhibits a more potent adjuvant activity than α-GalCer. In FIG. 2, the number of IFN secreting CD8+ T cells per million splenocytes is greater for CRONY 101 than for α-GalCer.

Thus, co-administration of α-C-GalCer to mice immunized with a suboptimal dose of a recombinant adenovirus expressing a malarial antigen enhanced protective antimalaria immunity and the level of malaria antigen-specific CD8$^+$ T-cell responses. Coadministration of 1 ng of CRONY 101 was compared to administration of 1 μg of α-GalCer. The administration of 1 ng of CRONY 101 resulted in the induction of ⅝-fold increased number of malaria specific CD8$^+$ cells, as compared to 1 μg of α-GalCer.

Further studies used a naked DNA plasmid encoding an HIV Gag sequence, as a vaccine. Coadministration of CRONY 101 with the DNA vaccine is expected to enhance the level of HIV-specific CD8$^+$ and CD4$^+$ T-cell responses with a a lesser dose compared to the dose needed for α-GalCer to display a similar level of adjuvant effect.

Figure 3A:
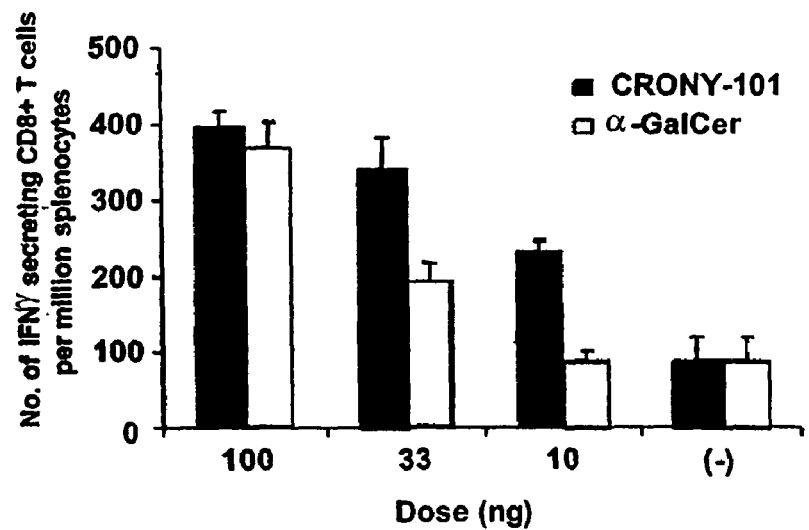
Figure 3B:
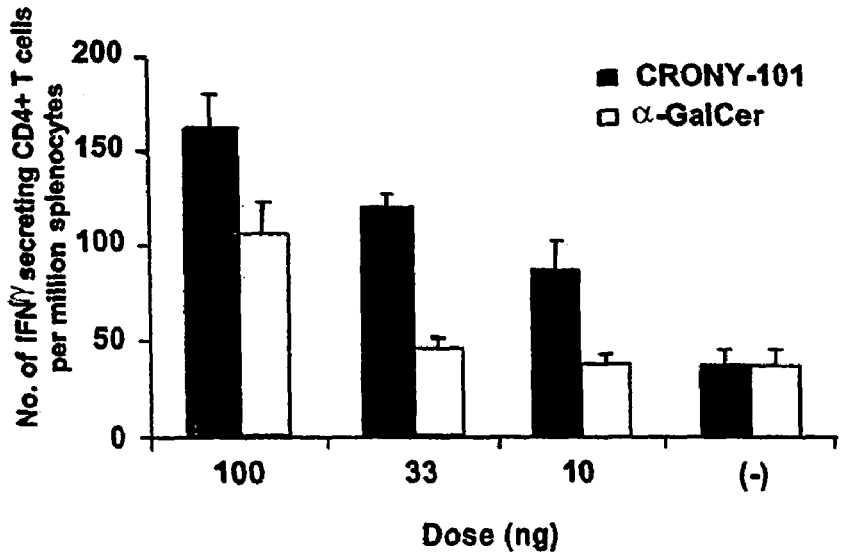

FIGS. 3A and 3B demonstrate the more potent adjuvant activity of CRONY 101 as compared to α-GalCer. FIG. 3A shows that CRONY 101 enhances a Gag-specific CD8+ T cell response elicited by a DNA vaccine encoding an HIV Gag sequence.

FIG. 3B shows that CRONY 101 exhibits more potent adjuvant activity than α-GalCer, enhancing Gag-specific CD4+ T cell response elicted by a DNA vaccine encoding a HIV-Gag sequence.

Since both CRONY 101 and α-GalCer stimulate human as well as murine NKT cells, it is expected that CRONY 101 will be useful as a more potent adjuvant than α-GalCer for the design of a novel, more efficient vaccine against malaria, and other intracellular pathogens as well as tumors and autoimmune diseases, the models in which CD8+ T-Cells have been shown to play a major protective role.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

All patents, applications, publications, test methods, literature, and protocols cited throughout this application, are incorporated herein by reference entireties for all purposes. In case of a conflict between material incorporated by reference and the present specification, the present specification controls.

What is claimed is:

1. A method for augmenting the immunogenicity of an antigen in a mammal, comprising immunizing the mammal with a composition comprising (i) the antigen and (ii) an adjuvant in an amount effective to augment the immunogenicity of said antigen, wherein the adjuvant comprises a compound of Formula I:

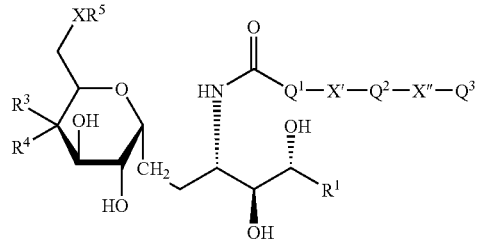

(I)

wherein X is O or NH;
$R^1$ is selected from the group consisting of —$(CH_2)_{11}CH_3$, —$(CH_2)_{12}CH_3$, —$(CH_2)_{13}CH_3$, —$(CH_2)_9CH(CH_3)_2$, —$(CH_2)_{10}CH(CH_3)_2$, —$(CH_2)_{11}CH(CH_3)_2$ and $(CH_2)_{11}CH(CH_3)$—$C_2H_5$;
$R^3$ is OH or a monosaccharide and $R^4$ is hydrogen, or $R^3$ is hydrogen and $R^4$ is OH or a monosaccharide;
$R^5$ is hydrogen or a monosaccharide;
$Q^1$ is optionally present and is a $C_{1-10}$ straight or branched chain alkylene, alkenylene, or alkynylene;
X' is optionally present and is O, S or $NR^8$;
$Q^2$ is optionally present and is a $C_{1-10}$ straight or branched chain alkylene, alkenylene or alkynylene;
X" is optionally present and is O, S or $NR^8$;
$Q^3$ is a straight or branched chain $C_{1-10}$ alkyl, alkenyl or alkynyl, or is hydrogen,
wherein each $Q^1$, $Q^2$ or $Q^3$ is optionally substituted with hydroxyl, halogen, cyano, nitro, $SO_2$, $NHR^8$, or C(=O)—$R^9$; and wherein
$R^8$ is hydrogen, $C_{1-5}$ alkyl, $C_{1-5}$ alkoxy, halogen, cyano, nitro, $SO_2$ or C(=O)—$R^9$;
$R^9$ is hydrogen, $C_{1-5}$ alkyl, $C_{1-5}$ alkoxy or $NHR^{10}$;
$R^{10}$ is hydrogen, $C_{1-5}$ alkyl or $C_{1-5}$ alkoxy;

a pharmaceutically acceptable salt thereof, or a pharmaceutically acceptable ester thereof, and wherein the effective amount of the adjuvant is in the range of 10-100 μg per kg of body weight.

2. The method of claim 1, wherein said antigen is malaria-specific.

3. The method of claim 2, wherein said malaria-specific antigen comprises irradiated plasmodial sporozoites.

4. The method of claim 2, wherein said malaria-specific antigen comprises a T cell epitope of the malarial circumsporozoite (CS) protein.

5. The method of claim 1, wherein said antigen is HIV-specific.

6. The method of claim 1, wherein said antigen is presented by a recombinant virus expressing said antigen.

7. The method of claim 6, wherein said virus is selected from the group consisting of a recombinant adenovirus, recombinant pox virus, and recombinant Sindbis virus.

8. The method of claim 1, wherein said mammal is human.

9. A method for enhancing or extending the duration of antigen-specific Th1-type immune responses in a mammal comprising administering to said mammal a composition comprising (i) an antigen and (ii) an adjuvant in an amount effective for enhancing or extending the duration of antigen-specific Th1-type immune responses comprising a compound of Formula (I)

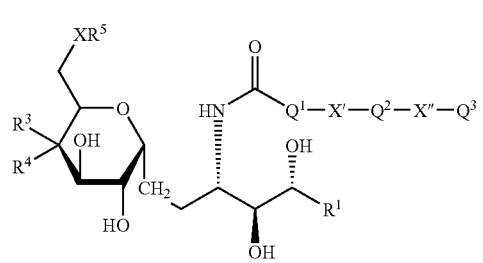

(I)

wherein X is O or NH;

$R^1$ is selected from the group consisting of —$(CH_2)_{11}CH_3$, —$(CH_2)_{12}CH_3$, —$(CH_2)_{13}CH_3$, —$(CH_2)_9CH(CH_3)_2$, —$(CH_2)_{10}CH(CH_3)_2$, —$(CH_2)_{11}CH(CH_3)_2$ and $(CH_2)_{11}CH(CH_3)$—$C_2H_5$;

$R^3$ is OH or a monosaccharide and $R^4$ is hydrogen, or $R^3$ is hydrogen and $R^4$ is OH or a monosaccharide;

$R^5$ is hydrogen or a monosaccharide;

$Q^1$ is optionally present and is a $C_{1-10}$ straight or branched chain alkylene, alkenylene, or alkynylene;

X' is optionally present and is O, S or $NR^8$;

$Q^2$ is optionally present and is a $C_{1-10}$ straight or branched chain alkylene, alkenylene or alkynylene;

X" is optionally present and is O, S or $NR^8$;

$Q^3$ is a straight or branched chain $C_{1-10}$ alkyl, alkenyl or alkynyl, or is hydrogen, wherein each $Q^1$, $Q^2$ or $Q^3$ is optionally substituted with hydroxyl, halogen, cyano, nitro, $SO_2$, $NHR^8$, or C(=O)—$R^9$; and wherein $R^8$ is hydrogen, $C_{1-5}$ alkyl, $C_{1-5}$ alkoxy, halogen, cyano, nitro, $SO_2$ or C(=O)—$R^9$;

$R^9$ is hydrogen, $C_{1-5}$ alkyl, $C_{1-5}$ alkoxy or $NHR^{10}$;

$R^{10}$ is hydrogen, $C_{1-5}$ alkyl or $C_{1-5}$ alkoxy;

a pharmaceutically acceptable salt thereof, or a pharmaceutically acceptable ester thereof, and wherein the effective amount of the adjuvant is in the range of 10-100 µg per kg of body weight.

10. The method of claim 9, wherein said Th1-type immune responses are CD8+ T cell responses.

11. A method for treating a disease in a mammal comprising administering to said mammal a composition comprising (i) an antigen and (ii) an adjuvant in an amount effective to treat the disease, the adjuvant comprising a glycosylceramide of the general Formula I:

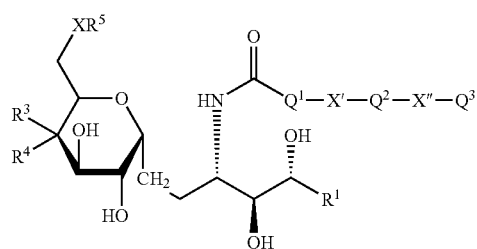

(I)

wherein X is O or NH;

$R^1$ is selected from the group consisting of —$(CH_2)_{11}CH_3$, —$(CH_2)_{12}CH_3$, —$(CH_2)_{13}CH_3$, —$(CH_2)_9CH(CH_3)_2$, —$(CH_2)_{10}CH(CH_3)_2$, —$(CH_2)_{11}CH(CH_3)_2$ and $(CH_2)_{11}CH(CH_3)$—$C_2H_5$;

$R^3$ is OH or a monosaccharide and $R^4$ is hydrogen, or $R^3$ is hydrogen and $R^4$ is OH or a monosaccharide;

$R^5$ is hydrogen or a monosaccharide;

$Q^1$ is optionally present and is a $C_{1-10}$ straight or branched chain alkylene, alkenylene, or alkynylene;

X' is optionally present and is O, S or $NR^8$;

$Q^2$ is optionally present and is a $C_{1-10}$ straight or branched chain alkylene, alkenylene or alkynylene;

X" is optionally present and is O, S or $NR^8$;

$Q^3$ is a straight or branched chain $C_{1-10}$ alkyl, alkenyl or alkynyl, or is hydrogen, wherein each $Q^1$, $Q^2$ or $Q^3$ is optionally substituted with hydroxyl, halogen, cyano, nitro, $SO_2$, $NHR^8$, or C(=O)—$R^9$; and wherein $R^8$ is hydrogen, $C_{1-5}$ alkyl, $C_{1-5}$ alkoxy, halogen, cyano, nitro, $SO_2$ or C(=O)—$R^9$;

$R^9$ is hydrogen, $C_{1-5}$ alkyl, $C_{1-5}$ alkoxy or $NHR^{10}$;

$R^{10}$ is hydrogen, $C_{1-5}$ alkyl or $C_{1-5}$ alkoxy;

a pharmaceutically acceptable salt thereof, or a pharmaceutically acceptable ester thereof, and wherein the effective amount of the adjuvant is in the range of 10-100 µg per kg of body weight.

12. The method of claim 11, wherein said disease is selected from the group consisting of infection and cancer.

13. The method of claim 12, wherein said infection is selected from the group consisting of viral infection, bacterial infection, parasitic infection, and fungal infection.

14. The method of claim 13, wherein said parasitic infection is malaria.

15. The method of claim 13, wherein said viral infection is HIV infection.

16. The method of claim 11, wherein said mammal is human.

17. A method for augmenting the protective immunity induced by an antigen in a mammal comprising administering to said mammal a pharmaceutical composition in an amount effective for augmenting the protective immunity induced by the antigen, wherein the pharmaceutical composition comprises (i) an immunogenically effective amount of an antigen and (ii) an immunogenically effective amount of an adjuvant comprising the compound of general Formula I:

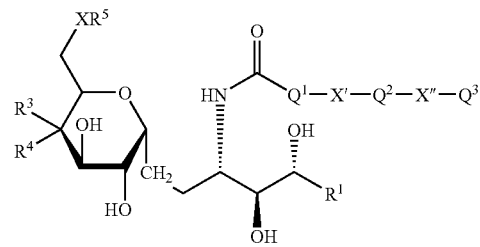

(I)

wherein X is O or NH;

$R^1$ is selected from the group consisting of —$(CH_2)_{11}CH_3$, —$(CH_2)_{12}CH_3$, —$(CH_2)_{13}CH_3$, —$(CH_2)_9CH(CH_3)_2$, —$(CH_2)_{10}CH(CH_3)_2$, —$(CH_2)_{11}CH(CH_3)_2$ and $(CH_2)_{11}CH(CH_3)$—$C_2H_5$;

$R^3$ is OH or a monosaccharide and $R^4$ is hydrogen, or $R^3$ is hydrogen and $R^4$ is OH or a monosaccharide;

$R^5$ is hydrogen or a monosaccharide;

$Q^1$ is optionally present and is a $C_{1-10}$ straight or branched chain alkylene, alkenylene, or alkynylene;

X' is optionally present and is O, S or $NR^8$;

$Q^2$ is optionally present and is a $C_{1-10}$ straight or branched chain alkylene, alkenylene or alkynylene;

X" is optionally present and is O, S or $NR^8$;

$Q^3$ is a straight or branched chain $C_{1-10}$ alkyl, alkenyl or alkynyl, or is hydrogen, wherein each $Q^1$, $Q^2$ or $Q^3$ is optionally substituted with hydroxyl, halogen, cyano, nitro, $SO_2$, $NHR^8$, or C(=O)—$R^9$; and wherein $R^8$ is hydrogen, $C_{1-5}$ alkyl, $C_{1-5}$ alkoxy, halogen, cyano, nitro, $SO_2$ or C(=O)—$R^9$;

$R^9$ is hydrogen, $C_{1-5}$ alkyl, $C_{1-5}$ alkoxy or $NHR^{10}$;

$R^{10}$ is hydrogen, $C_{1-5}$ alkyl or $C_{1-5}$ alkoxy;

a pharmaceutically acceptable salt thereof, or a pharmaceutically acceptable ester thereof and wherein the effective amount of the adjuvant is in the range of 10-100 μg per kg of body weight.

18. The method of claim 17, wherein the pharmaceutical composition further comprises a pharmaceutically acceptable carrier or excipient.

19. A method for treating a disease comprising administering to a human in need thereof a pharmaceutical composition comprising (i) an immunogenically effective amount of an antigen and (ii) an immunogenically effective amount of an adjuvant comprising the compound of general Formula I:

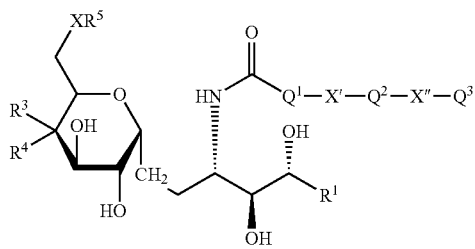

wherein X is O or NH;
R$^1$ is selected from the group consisting of —(CH$_2$)$_{11}$CH$_3$, —(CH$_2$)$_{12}$CH$_3$, —(CH$_2$)$_{13}$CH$_3$, —(CH$_2$)$_9$CH(CH$_3$)$_2$, —(CH$_2$)$_{10}$CH(CH$_3$)$_2$, —(CH$_2$)$_{11}$CH(CH$_3$)$_2$ and (CH$_2$)$_{11}$CH(CH$_3$)—C$_2$H$_5$;
R$^3$ is OH or a monosaccharide and R$^4$ is hydrogen, or R$^3$ is hydrogen and R$^4$ is OH or a monosaccharide;
R$^5$ is hydrogen or a monosaccharide;
Q$^1$ is optionally present and is a C$_{1-10}$ straight or branched chain alkylene, alkenylene, or alkynylene;
X' is optionally present and is O, S or NR$^8$;
Q$^2$ is optionally present and is a C$_{1-10}$ straight or branched chain alkylene, alkenylene or alkynylene;
X" is optionally present and is O, S or NR$^8$;
Q$^3$ is a straight or branched chain C$_{1-10}$ alkyl, alkenyl or alkynyl, or is hydrogen,
wherein each Q$^1$, Q$^2$ or Q$^3$ is optionally substituted with hydroxyl, halogen, cyano, SO$_2$, NHR$^8$, or C(=O)—R$^9$; and wherein
R$^8$ is hydrogen, C$_{1-5}$ alkyl, C$_{1-5}$ alkoxy, halogen, cyano, nitro, SO$_2$ or C(=O)—R$^9$;
R$^9$ is hydrogen, C$_{1-5}$ alkyl, C$_{1-5}$ alkoxy or NHR$^{10}$;
R$^{10}$ is hydrogen, C$_{1-5}$ alkyl or C$_{1-5}$ alkoxy;
a pharmaceutically acceptable salt thereof, or a pharmaceutically acceptable ester thereof and wherein the effective amount of the adjuvant is in the range of 10-100 μg per kg of body weight.

20. The method of claim 19, wherein said disease is selected from the group consisting of infection and cancer.

21. The method of claim 20, wherein said infection is selected from the group consisting of viral infection, bacterial infection, parasitic infection, and fungal infection.

22. The method of claim 21, wherein said parasitic infection is malaria.

23. The method of claim 21, wherein said viral infection is HIV infection.

24. A method for conferring immunity against the sporozoite stage of malaria to a susceptible mammalian host comprising administering to said host a composition comprising
(i) at least one malaria-specific antigen comprising a sporozoite surface antigen in a first amount, and (ii) a compound of Formula I:

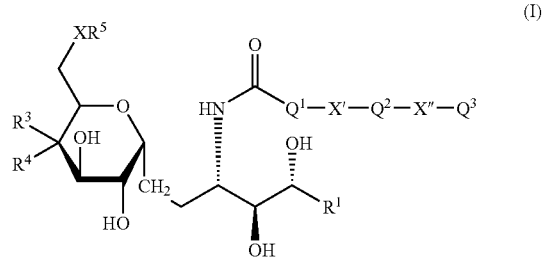

wherein X is O or NH;
R$^1$ is selected from the group consisting of —(CH$_2$)$_{11}$CH$_3$, —(CH$_2$)$_{12}$CH$_3$, —(CH$_2$)$_{13}$CH$_3$, —(CH$_2$)$_9$CH(CH$_3$)$_2$, —(CH$_2$)$_{10}$CH(CH$_3$)$_2$, —(CH$_2$)$_{11}$CH(CH$_3$)$_2$ and (CH$_2$)$_{11}$CH(CH$_3$)—C$_2$H$_5$;
R$^3$ is OH or a monosaccharide and R$^4$ is hydrogen, or R$^3$ is hydrogen and R$^4$ is OH or a monosaccharide;
R$^5$ is hydrogen or a monosaccharide;
Q$^1$ is optionally present and is a C$_{1-10}$ straight or branched chain alkylene, alkenylene, or alkynylene;
X' is optionally present and is O, S or NR$^8$;
Q$^2$ is optionally present and is a C$_{1-10}$ straight or branched chain alkylene, alkenylene or alkynylene;
X" is optionally present and is O, S or NR$^8$;
Q$^3$ is a straight or branched chain C$_{1-10}$ alkyl, alkenyl or alkynyl, or is hydrogen, wherein each Q$^1$, Q$^2$ or Q$^3$ is optionally substituted with hydroxyl, halogen, cyano, nitro, SO$_2$, NHR$^8$, or C(=O)—R$^9$; and wherein
R$^8$ is hydrogen, C$_{1-5}$ alkyl, C$_{1-5}$ alkoxy, halogen, cyano, nitro, SO$_2$ or C(=O)—R$^9$;
R$^9$ is hydrogen, C$_{1-5}$ alkyl, C$_{1-5}$ alkoxy or NHR$^{10}$;
R$^{10}$ is hydrogen, C$_{1-5}$ alkyl or C$_{1-5}$ alkoxy;
a pharmaceutically acceptable salt thereof, or a pharmaceutically acceptable ester thereof,
as an immune adjuvant in a second amount;
said first and second amounts being effective in combination to enhance or prolong the immune response mounted against said antigen by the host compared to the immune response that the host could have mounted upon the administration of said first amount of said antigen without the conjoint administration of said adjuvant, wherein said second amount is in the range of 10-100 μg per kg of body weight.

25. The method of claim 24, wherein said malaria-specific antigen comprises a T cell epitope of the plasmodial circumsporozoite (CS) protein.

26. The method of claim 25, wherein said T cell epitope has an amino acid sequence selected from the group consisting of YNRNIVNRLLGDALNGKPEEK (SEQ ID NO: 1), SYVPSAEQI (SEQ ID NO: 2), NVDPNANP (SEQ ID NO: 3), and EYLNKIQNSLSTEWSPC SVT (SEQ ID NO: 4).

27. The method of claim 24, wherein said malaria-specific antigen comprises a B cell epitope of the plasmodial circumsporozoite (CS) protein.

28. The method of claim 27, wherein said B cell epitope has an amino acid sequence (NANP)3 (SEQ ID NO: 15).

29. The method of claim 24, wherein said malaria-specific antigen is presented by a recombinant virus expressing said antigen.

30. The method of claim 29, wherein said virus is selected from the group consisting of a recombinant adenovirus, recombinant pox virus, and recombinant Sindbis virus.

31. The method of claim 24, wherein said host is human.

32. The method of claim 24, wherein said enhancement or extension of the immune response is manifested by the enhancement or extension of the duration of antigen-specific CD8+ T cell responses.

33. A method for enhancing a T cell response to an HIV antigen in a susceptible mammalian host comprising administering to said host a composition comprising:
(i) at least one HIV-specific antigen selected from the group consisting of Gag, Tat, Pol, Env, Nef, gp160, p18, and gp120 in a first amount, and
(ii) a compound of Formula I

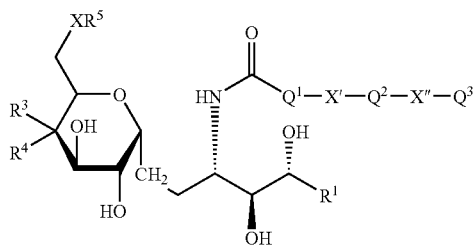

wherein X is O or NH;
$R^1$ is selected from the group consisting of $-(CH_2)_{11}CH_3$, $-(CH_2)_{12}CH_3$, $-(CH_2)_{13}CH_3$, $-(CH_2)_9CH(CH_3)_2$, $-(CH_2)_{10}CH(CH_3)_2$, $-(CH_2)_{11}CH(CH_3)_2$ and $(CH_2)_{11}CH(CH_3)-C_2H_5$;
$R^3$ is OH or a monosaccharide and $R^4$ is hydrogen, or $R^3$ is hydrogen and $R^4$ is OH or a monosaccharide;
$R^5$ is hydrogen or a monosaccharide;
$Q^1$ is optionally present and is a $C_{1-10}$ straight or branched chain alkylene, alkenylene, or alkynylene;
X' is optionally present and is O, S or $NR^8$;
$Q^2$ is optionally present and is a $C_{1-10}$ straight or branched chain alkylene, alkenylene or alkynylene;
X" is optionally present and is O, S or $NR^8$;
$Q^3$ is a straight or branched chain $C_{1-10}$ alkyl, alkenyl or alkynyl, or is hydrogen,
wherein each $Q^1$, $Q^2$ or $Q^3$ is optionally substituted with hydroxyl, halogen, cyano, nitro, $SO_2$, $NHR^8$, or $C(=O)-R^9$; and wherein
$R^8$ is hydrogen, $C_{1-5}$ alkyl, $C_{1-5}$ alkoxy, halogen, cyano, nitro, $SO_2$ or $C(=O)-R^9$;
$R^9$ is hydrogen, $C_{1-5}$ alkyl, $C_{1-5}$ alkoxy or $NHR^{10}$;
$R^{10}$ is hydrogen, $C_{1-5}$ alkyl or $C_{1-5}$ alkoxy;
a pharmaceutically acceptable salt thereof, or a pharmaceutically acceptable ester thereof,
as an immune adjuvant in a second amount;
said first and second amounts being effective in combination to enhance said T cell response mounted against said antigen by the host compared to the immune response that the host could have mounted upon the administration of said first amount of said antigen without the conjoint administration of said adjuvant, wherein said second amount is in the range of 10-100 µg per kg of body weight.

34. The method of claim 33, wherein said HIV-specific antigen comprises a T cell epitope of the Gag, Tat, Env, Pol, Nef, gp160, p18, or gp120.

35. The method of claim 34, wherein said T cell epitope has an amino acid sequence selected from the group consisting of RGPGRAFVTI (SEQ ID NO: 5), KAFSPEVIPMF (SEQ ID NO: 6), KAFSPEVI (SEQ ID NO: 7), TPQDLNMML (SEQ ID NO: 8), TPQDLNTML (SEQ ID NO: 9), DTINEEAAEW (SEQ ID NO: 10), KRWIILGLNK (SEQ ID NO: 11), and QATQEVKNW (SEQ ID NO: 12), RLRPGGKKK (SEQ ID NO: 13), and SLYNTVATL (SEQ ID NO: 14).

36. The method of claim 33, wherein said HIV-specific antigen is presented by a recombinant virus expressing said antigen.

37. The method of claim 33, wherein said virus is selected from the group consisting of a recombinant adenovirus, recombinant pox virus, and recombinant Sindbis virus.

38. The method of claim 33, wherein said host is human.

* * * * *

SEQUENCE LISTING

<160> NUMBER OF SEQ ID NOS: 16

<210> SEQ ID NO 1
<211> LENGTH: 21
<212> TYPE: PRT
<213> ORGANISM: P. yoelii

<400> SEQUENCE: 1

Tyr Asn Arg Asn Ile Val Asn Arg Leu Leu Gly Asp Ala Leu Asn Gly
1               5                   10                  15

Lys Pro Glu Glu Lys
            20

<210> SEQ ID NO 2
<211> LENGTH: 9
<212> TYPE: PRT
<213> ORGANISM: P. yoelii

<400> SEQUENCE: 2

Ser Tyr Val Pro Ser Ala Glu Gln Ile
1               5

<210> SEQ ID NO 3
<211> LENGTH: 8
<212> TYPE: PRT
<213> ORGANISM: P. falciparum

<400> SEQUENCE: 3

Asn Val Asp Pro Asn Ala Asn Pro
1               5

<210> SEQ ID NO 4
<211> LENGTH: 20
<212> TYPE: PRT
<213> ORGANISM: P. falciparum

<400> SEQUENCE: 4

Glu Tyr Leu Asn Lys Ile Gln Asn Ser Leu Ser Thr Glu Trp Ser Pro
1               5                   10                  15

Cys Ser Val Thr
            20

<210> SEQ ID NO 5
<211> LENGTH: 10
<212> TYPE: PRT
<213> ORGANISM: HIV-1

<400> SEQUENCE: 5

Arg Gly Pro Gly Arg Ala Phe Val Thr Ile
1               5                   10

<210> SEQ ID NO 6
<211> LENGTH: 11
<212> TYPE: PRT
<213> ORGANISM: HIV-1

<400> SEQUENCE: 6

Lys Ala Phe Ser Pro Glu Val Ile Pro Met Phe
1               5                   10

<210> SEQ ID NO 7
<211> LENGTH: 8

-continued

<212> TYPE: PRT
<213> ORGANISM: HIV-1

<400> SEQUENCE: 7

Lys Ala Phe Ser Pro Glu Val Ile
1               5

<210> SEQ ID NO 8
<211> LENGTH: 9
<212> TYPE: PRT
<213> ORGANISM: HIV-1

<400> SEQUENCE: 8

Thr Pro Gln Asp Leu Asn Met Met Leu
1               5

<210> SEQ ID NO 9
<211> LENGTH: 9
<212> TYPE: PRT
<213> ORGANISM: HIV-1

<400> SEQUENCE: 9

Thr Pro Gln Asp Leu Asn Thr Met Leu
1               5

<210> SEQ ID NO 10
<211> LENGTH: 10
<212> TYPE: PRT
<213> ORGANISM: HIV-1

<400> SEQUENCE: 10

Asp Thr Ile Asn Glu Glu Ala Ala Glu Trp
1               5                   10

<210> SEQ ID NO 11
<211> LENGTH: 10
<212> TYPE: PRT
<213> ORGANISM: HIV-1

<400> SEQUENCE: 11

Lys Arg Trp Ile Ile Leu Gly Leu Asn Lys
1               5                   10

<210> SEQ ID NO 12
<211> LENGTH: 9
<212> TYPE: PRT
<213> ORGANISM: HIV-1

<400> SEQUENCE: 12

Gln Ala Thr Gln Glu Val Lys Asn Trp
1               5

<210> SEQ ID NO 13
<211> LENGTH: 9
<212> TYPE: PRT
<213> ORGANISM: HIV-1

<400> SEQUENCE: 13

Arg Leu Arg Pro Gly Gly Lys Lys Lys
1               5

<210> SEQ ID NO 14
<211> LENGTH: 9
<212> TYPE: PRT
<213> ORGANISM: HIV-1

```
<400> SEQUENCE: 14

Ser Leu Tyr Asn Thr Val Ala Thr Leu
1               5

<210> SEQ ID NO 15
<211> LENGTH: 12
<212> TYPE: PRT
<213> ORGANISM: P. falciparum

<400> SEQUENCE: 15

Asn Ala Asn Pro Asn Ala Asn Pro Asn Ala Asn Pro
1               5                   10

<210> SEQ ID NO 16
<211> LENGTH: 9
<212> TYPE: PRT
<213> ORGANISM: influenza A virus

<400> SEQUENCE: 16

Thr Tyr Gln Arg Thr Arg Ala Leu Val
1               5
```